United States Patent
Nakano et al.

(10) Patent No.: US 8,942,460 B2
(45) Date of Patent: Jan. 27, 2015

(54) MEDICAL IMAGE PROCESSING APPARATUS THAT NORMALIZES A DISTANCE BETWEEN AN INNER WALL AND OUTER WALL OF THE MYOCARDIAL REGION

(75) Inventors: Fumiki Nakano, Utsonomiya (JP); Tomohiro Kawasaki, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 128 days.

(21) Appl. No.: 13/523,132

(22) Filed: Jun. 14, 2012

(65) Prior Publication Data

US 2012/0263368 A1    Oct. 18, 2012

Related U.S. Application Data

(63) Continuation of application No. PCT/JP2012/055240, filed on Mar. 1, 2012.

(30) Foreign Application Priority Data

Mar. 9, 2011   (JP) ................................. 2011-051396

(51) Int. Cl.
   *G06K 9/00*   (2006.01)
   *G06T 11/20*  (2006.01)
   (Continued)

(52) U.S. Cl.
   CPC .............. *G06T 11/206* (2013.01); *A61B 6/032* (2013.01); *A61B 6/037* (2013.01); *A61B 6/503* (2013.01); *A61B 6/5217* (2013.01); *A61B 6/5235* (2013.01); *A61B 6/5247* (2013.01);
   (Continued)

(58) Field of Classification Search
   None
   See application file for complete search history.

(56) References Cited

U.S. PATENT DOCUMENTS

| | | | |
|---|---|---|---|
| 7,945,080 B2 * | 5/2011 | Rinck et al. .................. | 382/131 |
| 2009/0005672 A1 | 1/2009 | Sugiura | |

(Continued)

FOREIGN PATENT DOCUMENTS

| | | |
|---|---|---|
| CN | 1914617 A | 2/2007 |
| CN | 101601071 A | 12/2009 |

(Continued)

OTHER PUBLICATIONS

Hubka, Michal, et al. "Three-dimensional echocardiographic measurement of left and right ventricular mass and volume: in vitro validation." The international journal of cardiovascular imaging 18.2 (2002): 111-118.*

(Continued)

*Primary Examiner* — Tahmina Ansari

(74) *Attorney, Agent, or Firm* — Oblon, Spivak, McClelland, Maier & Neustadt, L.L.P.

(57) ABSTRACT

According to one embodiment, storage unit stores three-dimensional function image data concerning a function index of the heart. The extraction unit extracts a myocardial region from the three-dimensional function image data. The normalization unit normalizes the distance between the inner wall and outer wall of the myocardial region with a predetermined numerical value range. The generation unit generates a bull's eye map expressing a spatial distribution of pixel values at positions on the myocardial region by two-dimensional polar coordinates. The positions correspond to predetermined values in the predetermined numerical value range. The display unit displays the bull's eye map.

8 Claims, 23 Drawing Sheets

(51) Int. Cl.
*A61B 6/03* (2006.01)
*A61B 6/00* (2006.01)
*A61B 8/08* (2006.01)

(52) U.S. Cl.
CPC .............. *A61B 8/0883* (2013.01); *A61B 8/483* (2013.01); *A61B 8/5261* (2013.01)
USPC .......................................................... 382/133

(56) References Cited

U.S. PATENT DOCUMENTS

| | | | |
|---|---|---|---|
| 2010/0074487 A1* | 3/2010 | Miyamoto et al. ............ | 382/128 |
| 2010/0201687 A1* | 8/2010 | Breeuwer et al. ............. | 345/424 |
| 2011/0306868 A1* | 12/2011 | Nagao .......................... | 600/410 |
| 2012/0263368 A1* | 10/2012 | Nakano et al. ................ | 382/133 |
| 2012/0323118 A1* | 12/2012 | Menon Gopalakrishna et al. ............................ | 600/431 |

FOREIGN PATENT DOCUMENTS

| | | |
|---|---|---|
| CN | 101796544 A | 8/2010 |
| EP | 2 130 490 A1 | 12/2009 |
| JP | 2006-075216 A | 3/2006 |
| JP | 2006-75216 A | 3/2008 |
| JP | 2008- 173236 A | 7/2008 |
| JP | 2008-173236 A | 7/2008 |
| JP | 2009-18005 A | 1/2009 |
| JP | 2009-28511 A | 2/2009 |
| JP | 2010-246776 A | 11/2010 |
| JP | 2010-537701 A | 12/2010 |
| JP | 2011-123045 A | 6/2011 |
| WO | 2008/111316 A1 | 9/2008 |

OTHER PUBLICATIONS

International Search Report issued Apr. 3, 2012, in PCT/JP2012/055240.
International Search Report mailed on Apr. 3, 2011, issued for International Application No. PCT/JP2012/055240, filed on Mar. 1, 2012 (with English translation of Categories).
International Written Opinion mailed on Apr. 3, 2011, issued for International Application No. PCT/JP2012/055240, filed on Mar. 1, 2012.
Office Action mailed Feb. 24, 2014, in Chinese Patent Application No. 201280000279.2 (with English-language Translation).
International Preliminary Report mailed Sep. 19, 2013, issued for International Application No. PCT/JP2012/055240, filed on Mar. 1, 2012 (English Translation).

* cited by examiner

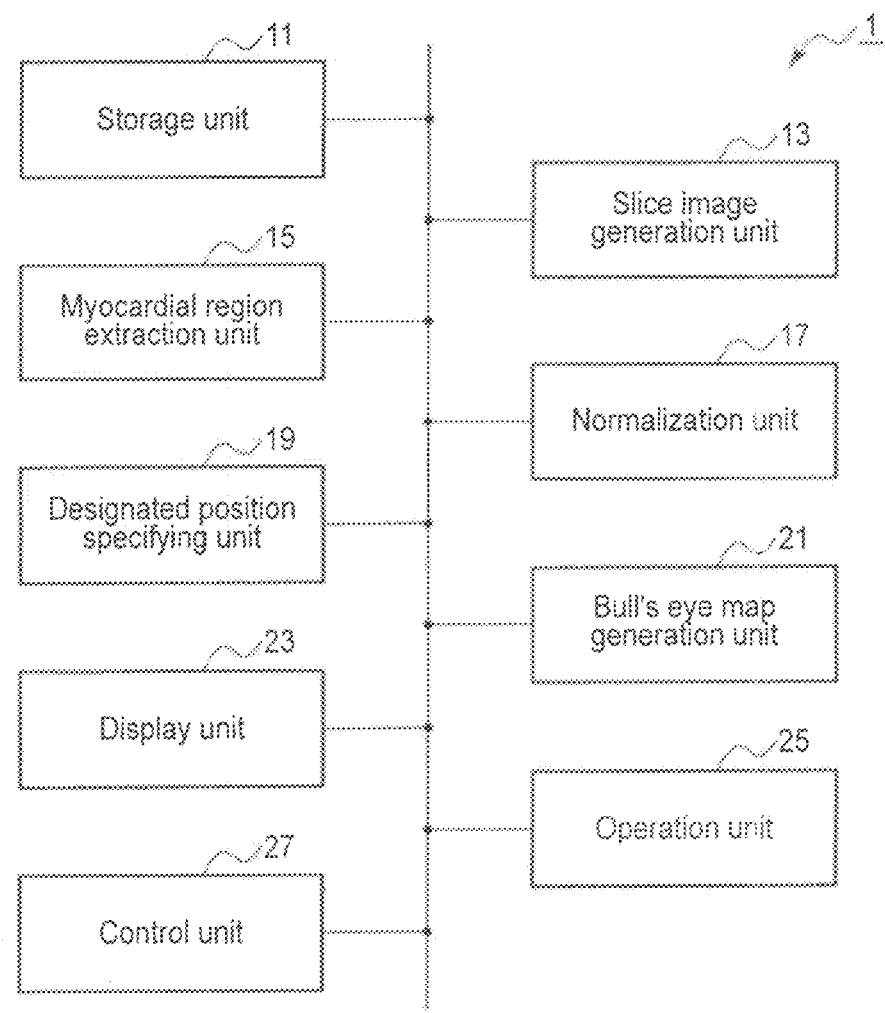
F I G. 1

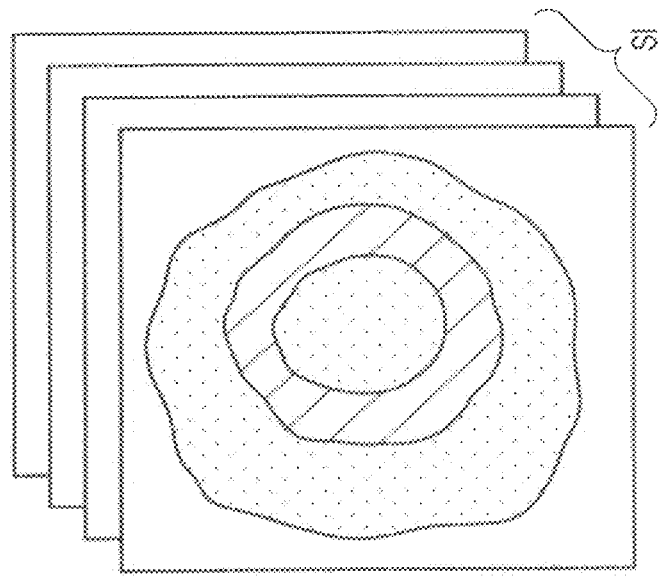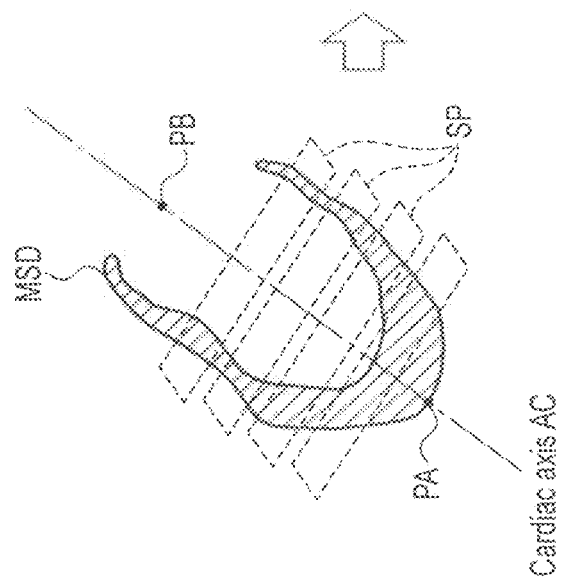
F I G. 3

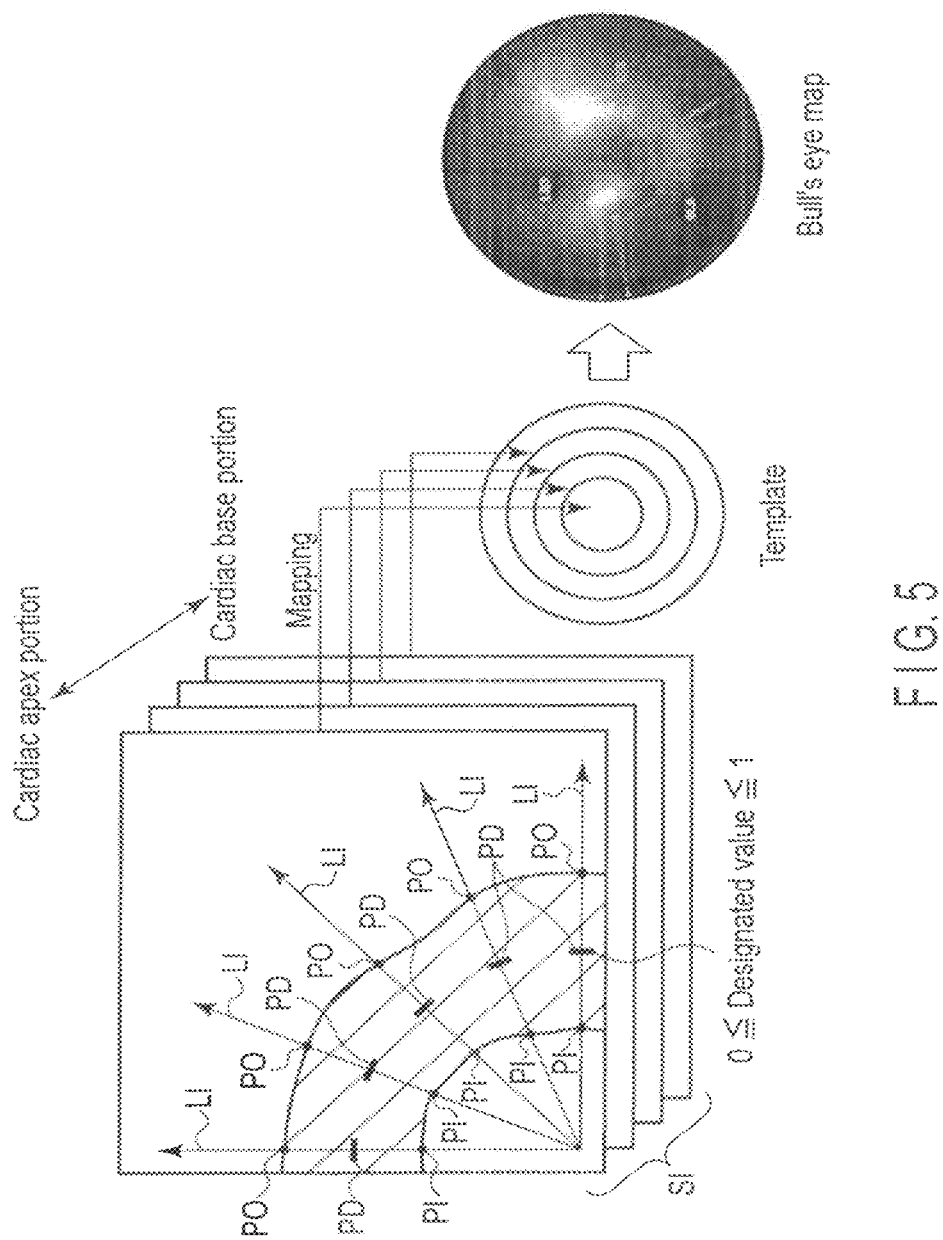
F I G. 5

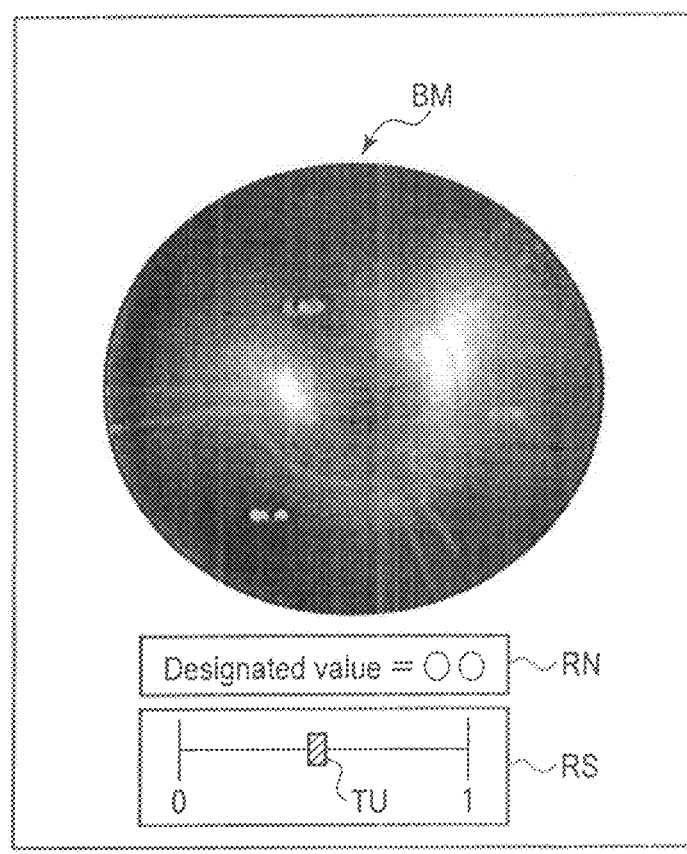
F I G. 6

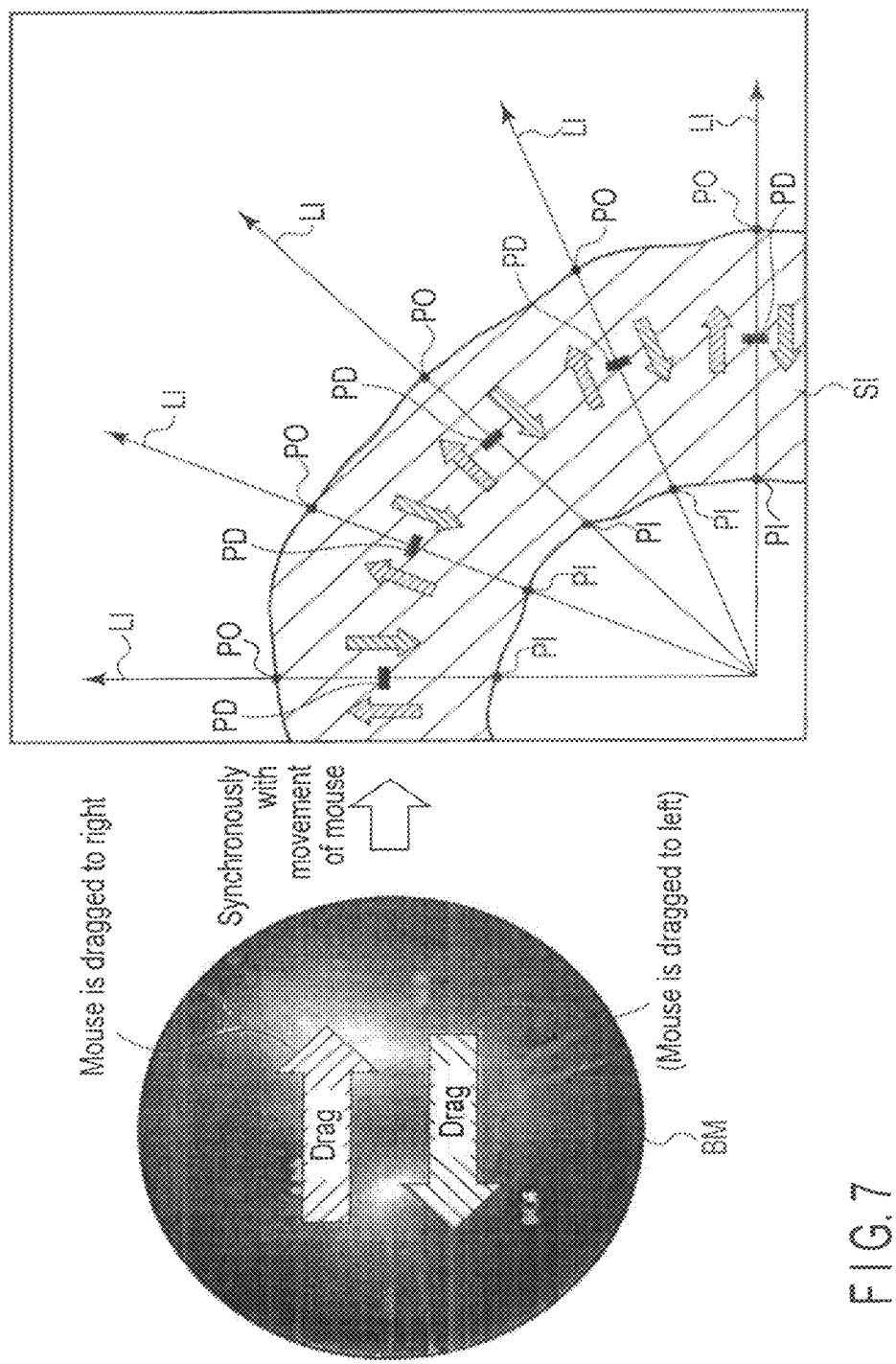
F I G. 7

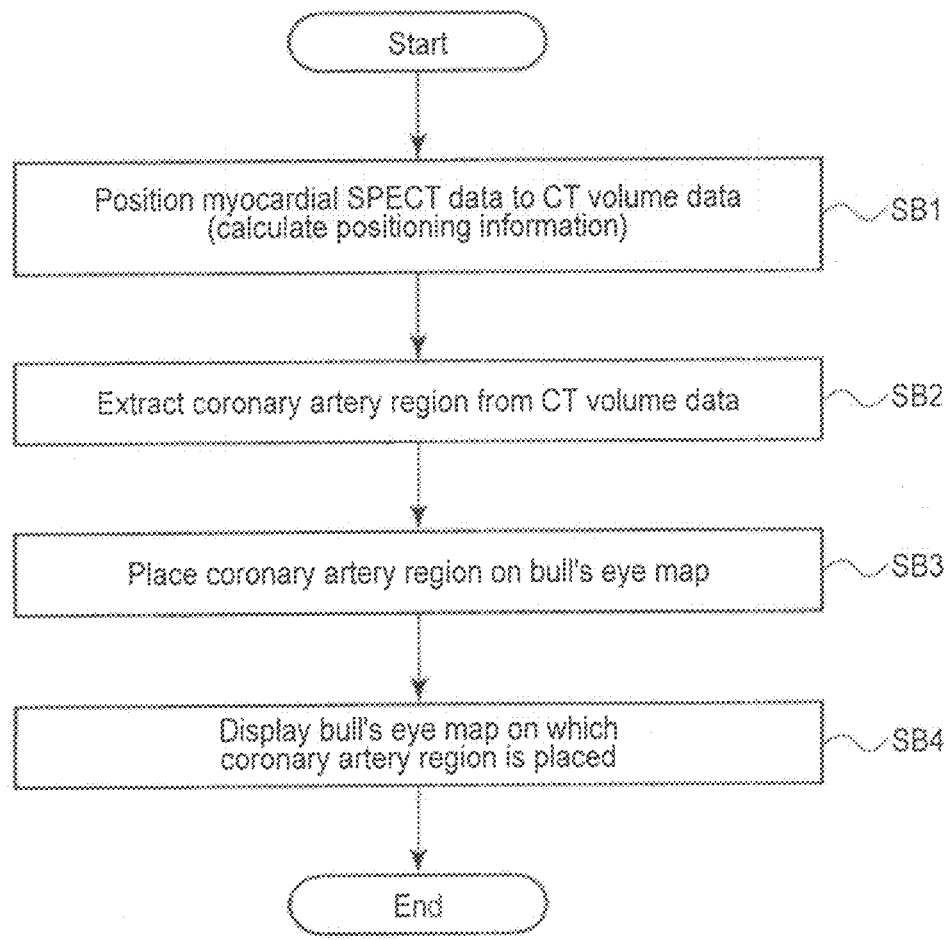
F I G. 9

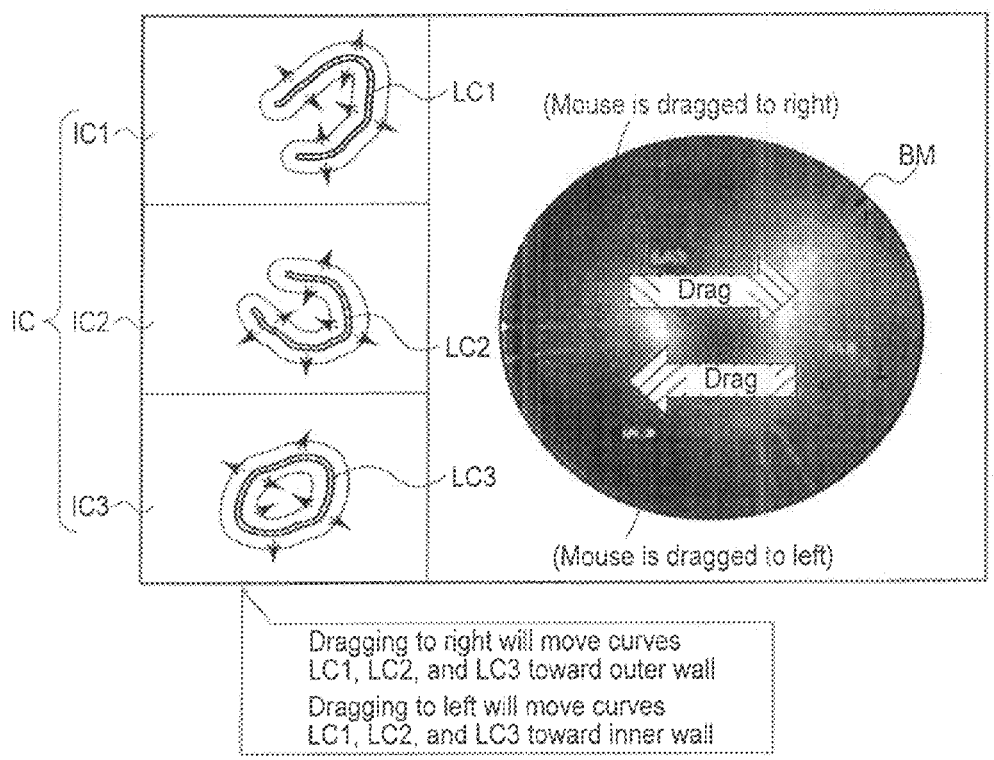
F I G. 15

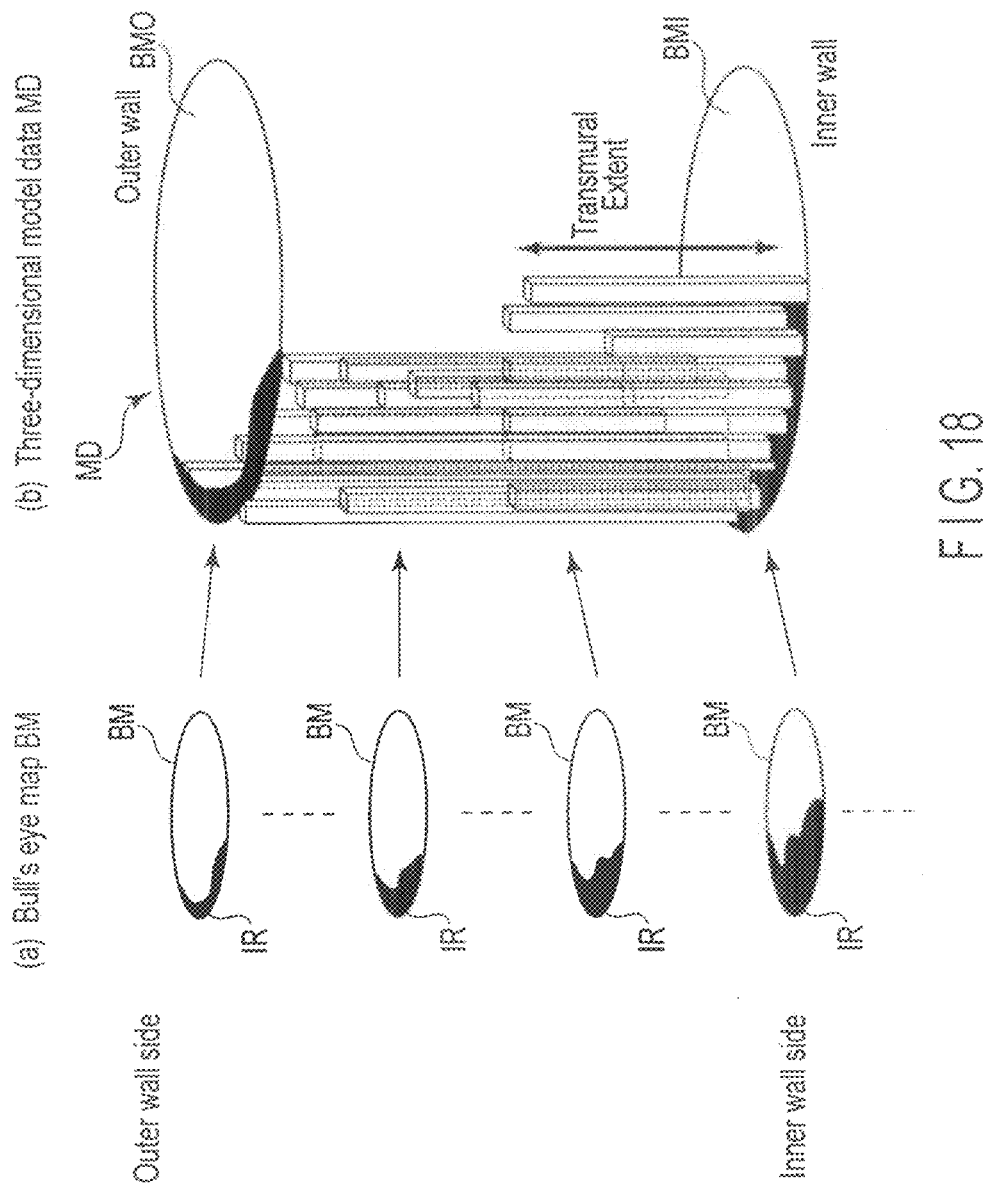
F I G. 18

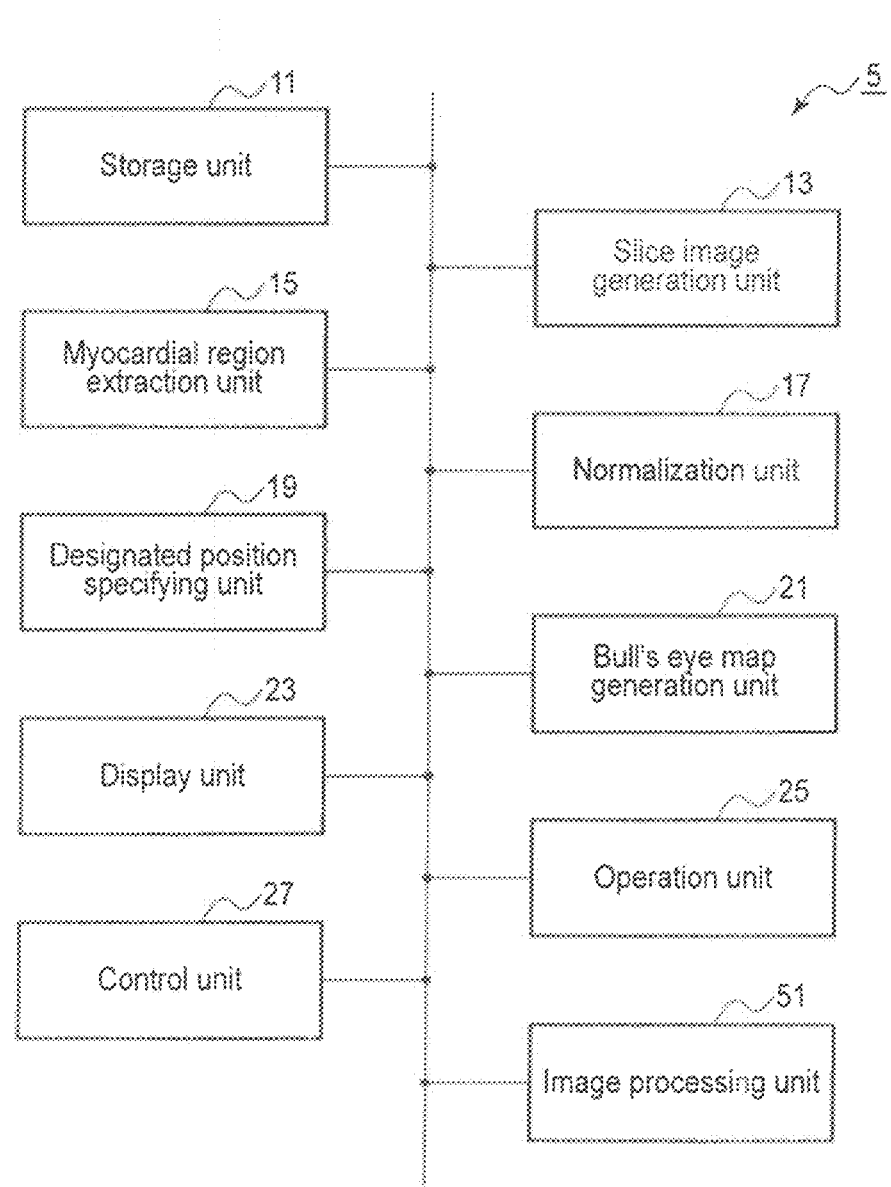
F I G. 20

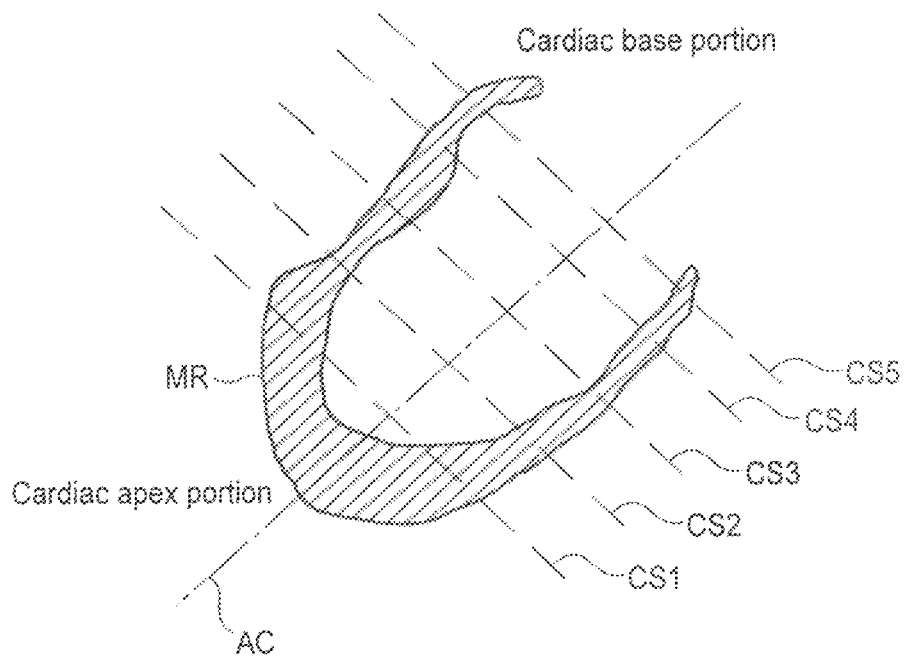
F I G. 21

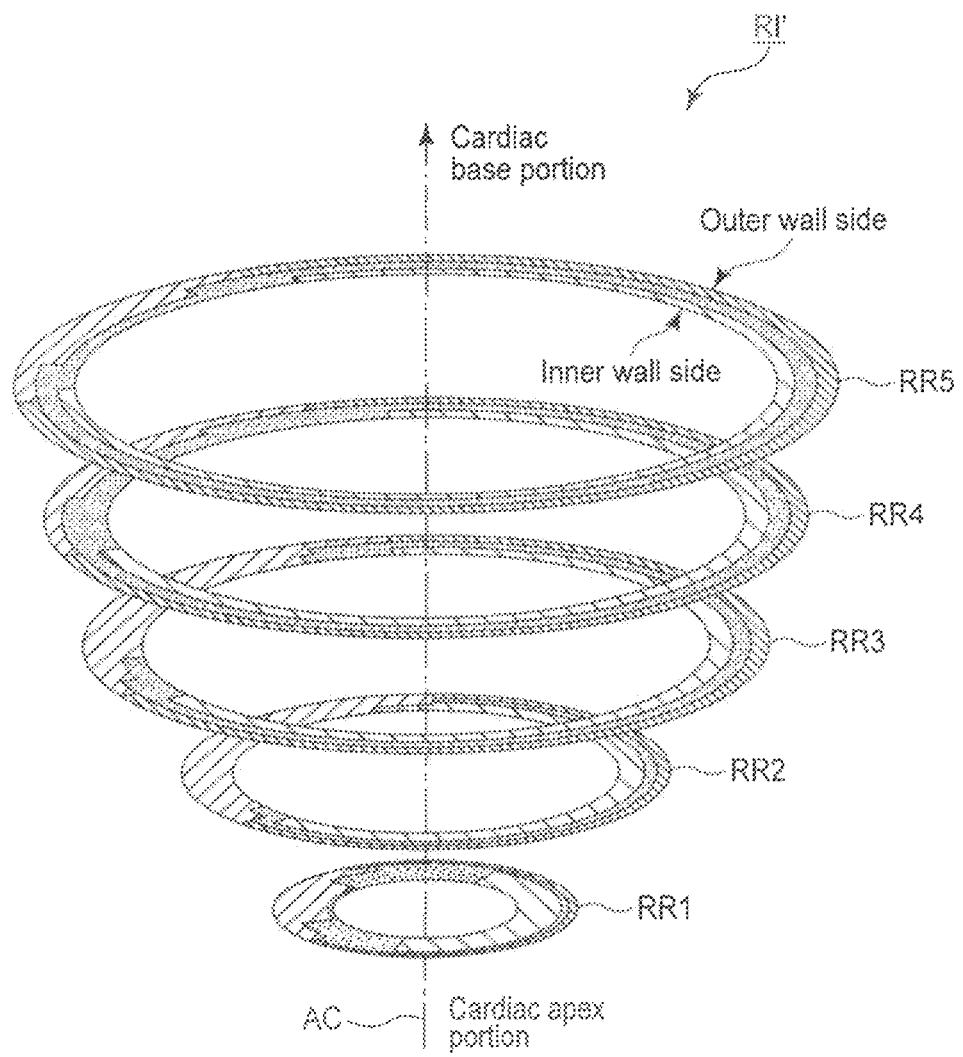
F I G. 23

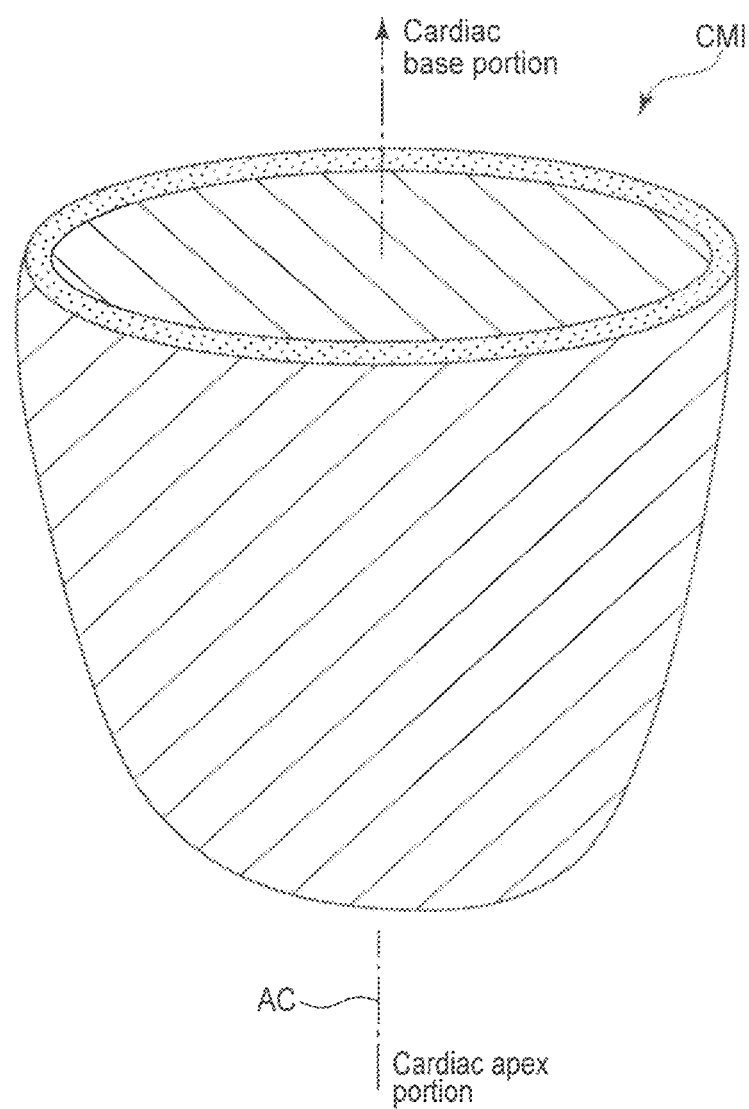
F I G. 24

US 8,942,460 B2

MEDICAL IMAGE PROCESSING APPARATUS THAT NORMALIZES A DISTANCE BETWEEN AN INNER WALL AND OUTER WALL OF THE MYOCARDIAL REGION

CROSS REFERENCE TO RELATED APPLICATIONS

This application is a Continuation Application of PCT Application No. PCT/JP2012/055240, filed Mar. 1, 2012 and based upon and claiming the benefit of priority from prior Japanese Patent Application No. 2011-051396, filed Mar. 9, 2011, the entire contents of all of which are incorporated herein by reference.

FIELD

Embodiments described herein relate generally to a medical image processing apparatus.

BACKGROUND

An ischemic cardiac disease is diagnosed by myocardial SPECT using a SPECT apparatus. Myocardial SPECT uses a bull's eye map. The following is a method of generating a bull's eye map. First of all, this method generates a plurality of short-axis slice images based on volume data acquired by a SPECT apparatus. In each short-axis slice image, a plurality of straight lines radially extending from the center point of a myocardial region are set. The method specifies the maximum value among the pixel values of a plurality of pixels on each straight line between the inner membrane and outer membrane of the myocardial region (the interior of the cardiac muscle). The method then assigns the specified maximum value to the pixel at the corresponding position on polar coordinates. This generates a bull's eye map. As described above, the maximum values on the straight lines extending through the interior of the cardiac muscle are assigned to a bull's eye map. It is therefore impossible to comprehend the pixel value distribution in the interior of the cardiac muscle by using a bull's eye map. This makes it difficult to determine the risk of an ischemic region when paying attention to a local region of the cardiac muscle.

It is an object of an embodiment to provide a medical image processing apparatus which can improve the diagnostic performance of a bull's eye map.

BRIEF DESCRIPTION OF THE DRAWINGS

FIG. 1 is a block diagram showing the arrangement of an image processing apparatus according to the first embodiment.

FIG. 3 is a view for explaining step SA1 in FIG. 2.
FIG. 5 is a view for explaining step SA5 in FIG. 2.
FIG. 6 is a view showing a display example of a bull's eye map in step SA7 in FIG. 2.
FIG. 7 is a view for explaining step SA8 in FIG. 2.

FIG. 9 is a flowchart showing a typical procedure for myocardial SPECT browsing display processing according to the second embodiment, which is performed under the control of a control unit in FIG. 8.

FIG. 15 is a view for explaining the movement of curves on CT slice images accompanying a change in designated value, which is performed by blood vessel placement in FIG. 12.

FIG. 18 is a view schematically showing a typical procedure for three-dimensional bull's eye map generation processing performed by a three-dimensional model generation unit in FIG. 17.

FIG. 20 is a block diagram showing the arrangement of a medical image processing apparatus according to the third modification.

FIG. 21 is a view for explaining an annular image generation processing by an image processing unit in FIG. 20.

FIG. 23 is a view showing an example of the three-dimensional annular image generated by the image processing unit in FIG. 20.

FIG. 24 is a view showing an example of the cup model image generated by the image processing unit in FIG. 20.

DETAILED DESCRIPTION

Figure 2:
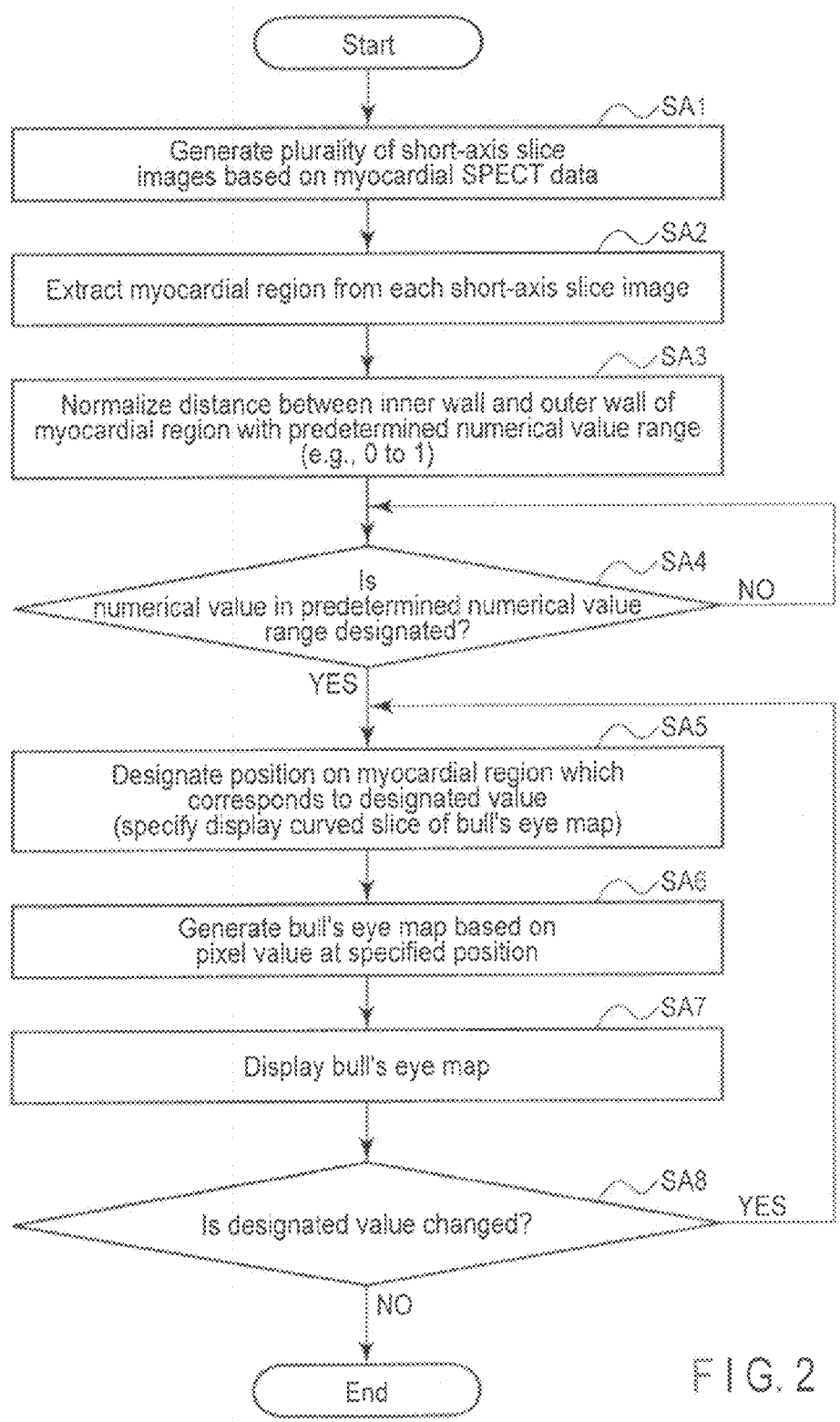
FIG. 2 is a flowchart showing a typical procedure for myocardial SPECT browsing display processing according to the first embodiment, which is performed under the control of a control unit in FIG. 1.

In general, according to one embodiment, a medical image processing apparatus includes a storage unit, a first extraction unit, a normalization unit, a bull's eye map generation unit, a display unit. A storage unit stores three-dimensional function image data concerning a function index of a heart. A first extraction unit extracts a myocardial region from the three-dimensional function image data. A normalization unit normalizes a distance between an inner wall and outer wall of the myocardial region with a predetermined numerical value range. A bull's eye map generation unit generates a bull's eye map expressing a spatial distribution of pixel values at positions on the myocardial region by two-dimensional polar coordinates. The positions correspond to predetermined values in the predetermined numerical value range. A display unit displays the bull's eye map.

A medical image processing apparatus according to an embodiment will be described below with reference to the accompanying drawings.

(First Embodiment)

FIG. 1 is a block diagram showing the arrangement of a medical image processing apparatus 1 according to the first embodiment. As shown in FIG. 1, the medical image processing apparatus 1 includes a storage unit 11, a slice image generation unit 13, a myocardial region extraction unit 15, a normalization unit 17, a designated position specifying unit 19, a bull's eye map generation unit 21, a display unit 23, an operation unit 25, and a control unit 27.

The storage unit 11 stores three-dimensional function image data concerning the function indices of the heart. It is possible to use, as three-dimensional function image data, those generated by medical image diagnostic apparatuses such as an X-ray computed tomography apparatus, magnetic resonance imaging apparatus, ultrasonic diagnostic apparatus, SPECT apparatus, and PET apparatus. The volume data generated by the SPECT apparatus or PET apparatus is assigned with the count values of gamma rays (or the index values of the function indices of the heart based on count values) emitted from radioactive isotopes accumulated in the cardiac muscle as pixel values. The volume data generated by the X-ray computed tomography apparatus, magnetic resonance imaging apparatus, or ultrasonic diagnostic apparatus is assigned with the index values of function indices concerning the motion function of the heart. For example, as function indices in the X-ray computed tomography apparatus or magnetic resonance imaging apparatus, there are known BP (a blood flow rate per unit volume or unit time in the myocardial tissue), BV (a blood flow rate per unit volume in the myocardial tissue), MTT (mean transit time), and the like. As a function index in the ultrasonic diagnostic apparatus, for example, the wall motion information of the cardiac muscle is known. As this wall motion information, for example, there are known information (radial-strain) concerning a change in the wall pressure direction, information (longitudinal-strain) concerning a change in the cardiac axis direction, information (circumferential-strain) concerning a change in the circumferential direction, information (rotation) concerning the region centroid in a short-axis slice, and information (torsion) as the rotation difference between different short-axis slices. Assume that a three-dimensional function image is the volume data (to be referred to as myocardial SPECT data hereinafter) generated by the SPECT apparatus using a myocardial SPECT technique. The pixel values of the pixels of myocardial SPECT data will be referred to as myocardial SPECT values. The storage unit 11 stores an image processing program for myocardial SPECT browsing display processing (to be described later).

The slice image generation unit 13 generates a plurality of short-axis slice images respectively corresponding to a plurality of short-axis slices arranged along the cardiac axis of a cardiac region or a specific region of the cardiac region based on myocardial SPECT data. A short-axis slice means a slice perpendicular to the cardiac axis.

The myocardial region extraction unit 15 extracts the specific region of a cardiac region from myocardial SPECT data. A specific region may be any anatomical region of the cardiac region. Assume that in the following description, a specific region is a clinically useful pixel region (to be referred to as a myocardial region hereinafter) concerning the cardiac muscle of the left ventricle. Typically, the myocardial region extraction unit 15 extracts a myocardial region from each of a plurality of short-axis slice images.

The normalization unit 17 normalizes the distance between the inner wall and outer wall of the myocardial region with a predetermined numerical value range. Typically, the normalization unit 17 normalizes the distance between the inner wall and outer wall of the myocardial region with a predetermined numerical value range with respect to each of a plurality of short-axis slice images. The user can arbitrarily set a numerical value range via the operation unit 25.

The designated position specifying unit 19 specifies a position on a myocardial region which corresponds to the designated value designated by the user within a predetermined numerical value range. The designated position specifying unit 19 specifies a position on the myocardial region which corresponds to the designated value designated by the user with respect to each of a plurality of short-axis slice images. The user arbitrarily sets a designated value in the predetermined numerical value range via the operation unit 25.

The bull's eye map generation unit 21 generates a bull's eye map expressing the spatial distribution of myocardial SPECT values at positions on a myocardial region which correspond to a designated value by using two-dimensional polar coordinates defined by rotational angles around the cardiac axis of the left ventricular region and distances from a reference point on the cardiac axis. Designated values correspond to display slice positions on a bull's eye map. Note that the display slices of the bull's eye map are curved surfaces in myocardial SPECT data defined by an orthogonal coordinate system. Therefore, the display slices of a bull's eye map will be referred to as display curved slices.

The display unit 23 displays the generated bull's eye map on a display device. As a display device, it is possible to use, for example, a CRT display, liquid crystal display, organic EL display, or plasma display, as needed.

The operation unit 25 inputs various kinds of instructions and information in accordance with instructions issued from the user via an input device. For example, the operation unit 25 designates a designated value in a predetermined numerical value range in accordance with an instruction issued by the user via an input device. As an input device, it is possible to use a pointing device such as a mouse or trackball, a selection device such as a mode switch, or an input device such as a keyboard, as needed.

The control unit 27 functions as the main unit of the medical image processing apparatus 1. The control unit 27 performs myocardial SPECT browsing display processing by reading out image processing programs stored in the storage unit 11 and controlling the respective units in accordance with the programs.

Myocardial SPECT browsing display processing performed under the control of the control unit 27 will be described in detail below. FIG. 2 is a flowchart showing a typical procedure for myocardial SPECT browsing display processing performed under the control of the control unit 27.

As shown in FIG. 2, the control unit 27 causes the slice image generation unit 13 to perform short-axis slice image generation processing in response to an instruction to start myocardial SPECT browsing display processing issued by the user via the operation unit 25 (step SA1). In step SA1, the slice image generation unit 13 generates a plurality of short-axis slice images respectively corresponding to a plurality of short-axis slices arranged along the cardiac axis of the Left ventricular region based on myocardial SPECT data.

FIG. 3 is a view for explaining step SA1. More specifically, first of all, the slice image generation unit 13 applies a region growing method (region growing) to myocardial SPECT data MSD for the extraction of a left ventricular region. The left ventricular region is a set of pixels falling within a myocardial SPECT value range which cardiac muscle can have. First of all, the slice image generation unit 13 sets a seed point in the left ventricular region in accordance with operation by the user via the operation unit 25 or by image processing. The slice image generation unit 13 then searches for 26 voxels adjacent to the seed point, and integrates adjacent voxels satisfying an integration condition. An integration condition is set in the myocardial SPECT value range which the left ventricle can have. This operation extracts a pixel region satisfying the integration condition and coupled to the seed point, i.e., the left ventricular region. Upon extracting the left ventricular region, the slice image generation unit 13 specifies a cardiac apex portion PA and a cardiac base portion PB of the left ventricular region in accordance with the shape of the extracted left ventricular region. The slice image generation unit 13 sets an axis connecting the cardiac apex portion PA and the cardiac base portion PB as a cardiac axis (short axis) AC. Upon setting the cardiac axis AC, the slice image generation unit 13 sets a plurality of short-axis slices SP arranged along the set cardiac axis AC. The slice image generation unit 13 then generates a plurality of slice images IS respectively corresponding to the plurality of set short-axis slices SP based on the myocardial SPECT data MSD. Each short-axis slice image IS expresses the spatial distribution of myocardial SPECT values on the short-axis slice SP by an orthogonal coordinate system. Each short-axis slice image IS includes the left ventricular region. The left ventricular region includes a myocardial region. Assume that the slice numbers of the short-axis slices SP are defined to be 1 to N (integers) from the cardiac apex portion PA to the cardiac base portion PB. N is defined to be the number of short-axis slices SP. The user can arbitrarily set N via the operation unit 25.

Upon executing step SA1, the control unit 27 causes the myocardial region extraction unit 15 to perform myocardial region extraction processing (step SA2). In step SA2, the myocardial region extraction unit 15 extracts a myocardial region from each short-axis slice image. More specifically, the myocardial region extraction unit 15 applies a region growing method to each short-axis slice image. A myocardial region is a set of pixels falling within the myocardial SPECT value range which the cardiac muscle can have. First of all, the myocardial region extraction unit 15 sets a seed point in the myocardial region in accordance with operation by the user via the operation unit 25 or by image processing. The myocardial region extraction unit 15 then searches for 26 voxels adjacent to the seed point, and integrates adjacent voxels satisfying an integration condition. An integration condition is set in the myocardial SPECT value range which the cardiac muscle can have. This operation extracts a pixel region satisfying the integration condition and coupled to the seed point, i.e., the myocardial region.

Upon executing step SA2, the control unit 27 causes the normalization unit 17 to perform normalization processing (step SA3). In step SA3, the normalization unit 17 normalizes the interval between the inner wall and outer wall of the myocardial region with a predetermined numerical value range.

Figure 4:
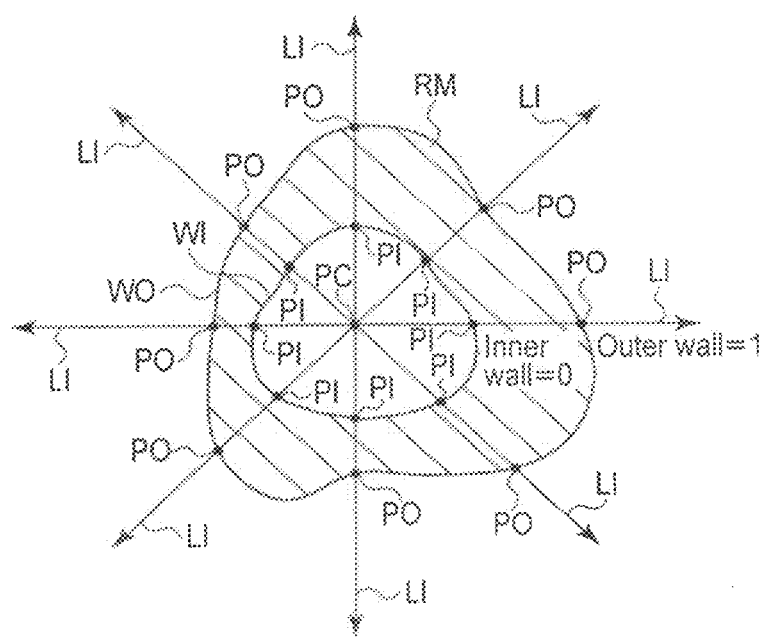
FIG. 4 is a view for explaining step SA3 in FIG. 2.

FIG. 4 is a view for explaining step SA3. FIG. 4 shows a myocardial region RM included in each short-axis slice image. More specifically, first of all, the normalization unit 17 extracts an inner wall WI and an outer wall WO of the myocardial region RM from each short-axis slice image. More specifically, the normalization unit 17 extracts a closed curve (inner wall) inside the myocardial region by tracing the inner boundary of the myocardial region RM, and extracts a closed curve (outer wall) outside the myocardial region by tracing the outer boundary of the myocardial region. The inner boundary is one of the two walls of the myocardial region RM which is closer to the cardiac axis. The outer boundary is one of the two walls of the myocardial region RM which is farther from the cardiac axis. Upon extraction of the inner closed curve (inner wall WI), the normalization unit 17 calculates the barycenter of the inner closed curve. Upon extraction of the outer closed curve, the normalization unit 17 calculates the barycenter of the outer closed curve (outer wall WO). The normalization unit 17 then calculates a center point PC between the barycenter of the inner closed curve and the barycenter of the outer closed curve. The calculated center point PC is handled as the center point of the myocardial region RM in each short-axis slice image. The normalization unit 17 sets a plurality of straight lines LI radially extending from the center point PC. In this case, numbers are assigned to the respective straight lines LI to identify them. The normalization unit 17 specifies intersection points PI between the straight lines LI and the inner wall WI and intersection points PO between the straight lines LI and the outer wall WO. The normalization unit 17 specifies the coordinates of the specified intersection points PI and PO on the short-axis slice image. Coordinates on the short-axis slice image are defined by an orthogonal coordinate system. The normalization unit 17 normalizes the distance between the intersection point PI and intersection point PO on each straight line LI with a predetermined numerical range. For example, a predetermined numerical value range is set to 0 to 1. In this case, the normalization unit 17 sets the position of the intersection point PI to 0, and the position of the intersection point PO to 1. The positions of the respective points on the straight line LI between the intersection point PI and the intersection point PO are set such that the distance from the intersection point PI to the position of each point linearly changes from 0 to 1 in the direction from the intersection point PI to the intersection point PO. With this operation, the distances are normalized. The position of each point defined by normalization will be referred to as a normalized position.

Upon executing step SA3, the control unit 27 stands by until the user designates a numerical value within a predetermined numerical value range via the operation unit 25 (step SA4). The user designates, as a designated value, a desired numerical value equal to or more than the lower limit and equal to less than the upper limit of the numerical value range via the operation unit 25. If the numerical value range is from 0 to 1, the user designates a desired numerical value equal to or more than 0 and equal to or less than 1 as a designated value. The user may directly input a numerical value as a designated value via an input device such as a keyboard or touch panel. Alternatively, the user may designate a desired value by using a slider bar and its knob. The slider bar corresponds to a numerical value range. The knob corresponds to a desired value. The user slides the knob on the slider bar via the input device. The control unit 27 holds a table associating the position of the knob on the slider bar with a designated value. The control unit 27 calculates a designated value corresponding to the position of the knob by using this table. Designating a designated value is synonymous with designating a display curved slice position on the bull's eye map.

Conventionally, the maximum myocardial SPECT value on each straight line is mapped on a bull's eye map. Such a conventional technique has no concept of a display curved slice on a bull's eye map.

When the user designates a designated value, the control unit 27 causes the designated position specifying unit 19 to perform designated position specifying processing (step SA5). In step SA5, the designated position specifying unit 19 specifies a position on the myocardial region which corresponds to the designated value designated in step SA4. More specifically, the designated position specifying unit 19 specifies the position (coordinates) of a pixel corresponding to the designated value with respect to each straight line on each short-axis slice image. The specified coordinates of the pixel are defined by an orthogonal coordinate system. More specifically, the designated position specifying unit 19 specifies the coordinates of a pixel corresponding to the designated value, the slice number of a short-axis slice to which the pixel belongs, and the number of a straight line to which the pixel belongs. Note that a designated value may be determined in advance.

Upon executing step SA5, the control unit 27 causes the bull's eye map generation unit 21 to perform bull's eye map generation processing (step SA6). In step SA6, the bull's eye map generation unit 21 generates a bull's eye map expressing the spatial distribution of myocardial SPECT values at the positions specified in step SA5 by using two-dimensional polar coordinates defined by rotational angles around the cardiac axis and distances from a reference point on the cardiac axis. As a reference point, a cardiac apex portion is typically used.

FIG. 5 is a view for explaining step SA6. Assume that the coordinates of a pixel corresponding to a designated value PD are specified on each straight line LI of each short-axis slice image IS, as shown in FIG. 5. First of all, the bull's eye map generation unit 21 specifies a myocardial SPECT value at the specified coordinates. The bull's eye map generation unit 21 generates a bull's eye map by assigning (mapping) the specified myocardial SPECT values to corresponding positions on a template. The center of the template corresponds to the cardiac apex portion of the left ventricular region. An outer edge of the template corresponds to the cardiac base portion of the left ventricular region. The distance from the center point of the template to each pixel corresponds to the slice number (slice position) of a short-axis slice. An angle around the center point of the template corresponds to an angle around the cardiac axis. That is, each pixel of the template one-to-one corresponds to each straight line LI. Each pixel of the template is uniquely specified by the slice number of a short-axis slice and the number of the straight line LI. Each pixel of the template is assigned with the myocardial SPECT value of a pixel, of the pixels on the straight line LI corresponding to the pixel, which corresponds to the designated value PD.

That is, the bull's eye map generation unit 21 specifies a pixel on the template which corresponds to the slice number and the number of the straight line LI specified in step SA5, and assigns the myocardial SPECT value of the pixel specified in step SA5 to the specified pixel on the template. Performing this processing for all the pixels on the template will generate a bull's eye map.

Upon executing step SA6, the control unit 27 causes the display unit 23 to perform display processing (step SA7). In step SA7, the display unit 23 displays the bull's eye map displayed in step SA6 on the display device.

FIG. 6 is a view showing a display example of a bull's eye map BM. As shown in FIG. 6, each pixel of the bull's eye map BM is displayed in a color corresponding to a myocardial SPECT value. More specifically, the display unit 23 holds a color table associating myocardial SPECT values with color values. The display unit 23 specifies a color value for each pixel of the bull's eye map generated in step SA6 by using the color table. The display unit 23 displays each pixel of the bull's eye map BM in a color corresponding to the specified color value.

Note that it is preferable to arrange a display region RN and a display region RS to present a designated value to the user. The display region RN displays the numerical value of a designated value. The display region RS displays a slider bar. A knob TU is superimposed on the slider bar at a position corresponding to a designated value. The user can comprehend a designated value by seeing the designated value or the position of the knob TU on the slider bar. Note that only one of the display region RN and the display region RS may be provided.

Upon executing step SA7, the control unit 27 stands by until the user changes a designated value via the operation unit 25 (step SA8). That is, the medical image processing apparatus 1 has a function of arbitrarily changing a display curved slice of the bull's eye map.

FIG. 7 is a view for explaining step SA8. As shown in FIG. 7, it is preferable to change the designated value PD in synchronism with the movement of an input device (mouse). More specifically, when the user drags the mouse to the right in a specific region on a display window (or an application window), the apparatus increases the designated value PD by a numerical value corresponding to the amount of drag in the rightward direction. When the user drags the mouse to the left in a specific region on a display window (or an application window), the apparatus decreases the designated value PD by a numerical value corresponding to the amount of drag to the right. It is preferable to set a specific region in a display region of the bull's eye map BM from the viewpoint of the operability of designated value changing operation by the user. The control unit 27 calculates a designated value after changing operation in accordance with the amount of drag and the dragging direction.

Note that the method of changing a designated value is not limited to the above method of changing a designated value in synchronism with the movement of an input device. For example, the user may change a designated value by directly inputting a numerical value via an input device such as a keyboard or touch panel or moving the position of the knob on the slider bar.

When the user changes a designated value (a display curved slice of the bull's eye map), the control unit 27 repeats steps SA5, SA6, and SA7 to generate a bull's eye map concerning the changed designated value. More specifically, in step SA5, the designated position specifying unit 19 specifies a position on a myocardial region which corresponds to the changed designated value set in step SA8. In step SA6, the bull's eye map generation unit 21 generates a bull's eye map concerning the changed designated value in accordance with a myocardial SPECT value at the specified position. In step SA7, the display unit 23 displays the bull's eye map concerning the changed designated value. The display unit 23 displays the bull's eye map concerning the changed designated value in real time accompanying a change in designated value.

As described above, the control unit 27 allows to arbitrarily change a designated value, i.e., a display curved slice of the bull's eye map, and displays the bull's eye map corresponding to the changed designated value in real time, thereby allowing browsing display of the bull's eye map.

If no designated value is changed, and, for example, the user has issued an instruction to terminate myocardial SPECT browsing display processing via the operation unit 25 (NO in step SA8), the control unit 27 terminates the myocardial SPECT browsing display processing in response to the instruction.

A user such as a doctor is not interested in only a maximum value in the thickness direction of a myocardial region. When diagnosing the presence/absence of an ischemic region, the user needs to observe myocardial SPECT values along the thickness direction of the myocardial region. The thickness of the myocardial region (the distance from the inner wall and the outer wall on each straight line) is not constant and varies depending on regions in the myocardial region. When designating a position in a myocardial region in the thickness direction with an absolute distance (distance before normalization), the distance to the inner wall is shorter than that to the outer wall in a given region, and the distance to the outer wall is shorter than that to the inner wall in another region.

With the above arrangement, the medical image processing apparatus 1 normalizes the thickness of a myocardial region with a predetermined numerical value range and generates a bull's eye map in accordance with myocardial SPECT values at positions corresponding to arbitrary designated values in this numerical value range. Performing normalization in this manner allows the medical image processing apparatus 1 to collectively designate anatomically homogeneous positions near the inner wall or outer wall or along the thickness direction of a myocardial region such as the interior of the cardiac muscle with a single designated value. That is, normalization makes it possible to handle a designated value as the position of a display curved slice of a bull's eye map. In addition, the medical image processing apparatus 1 can arbitrarily change a designated value in accordance with an instruction from the user, and hence can arbitrarily change a display curved slice of a bull's eye map. This allows the medical image processing apparatus 1 to perform browsing display of the spatial distribution of myocardial SPECT values at arbitrary positions in a myocardial region along the thickness direction with a bull's eye map. Browsing display allows to examine a region in a wide range in a short period of time, thereby implementing, for example, quick diagnosis of the presence/absence of an ischemic region or early detection of an ischemic region.

As described above, the medical image processing apparatus according to the first embodiment can achieve an improvement in the diagnostic performance of a bull's eye map.

(Second Embodiment)

A medical image processing apparatus according to the second embodiment superimposes and displays a blood vessel region on a bull's eye map. The medical image processing apparatus according to the second embodiment will be described below. Note that the same reference numerals in the following description denote constituent elements having almost the same functions as those in the first embodiment, and a repetitive description will be made only when required.

Figure 8:
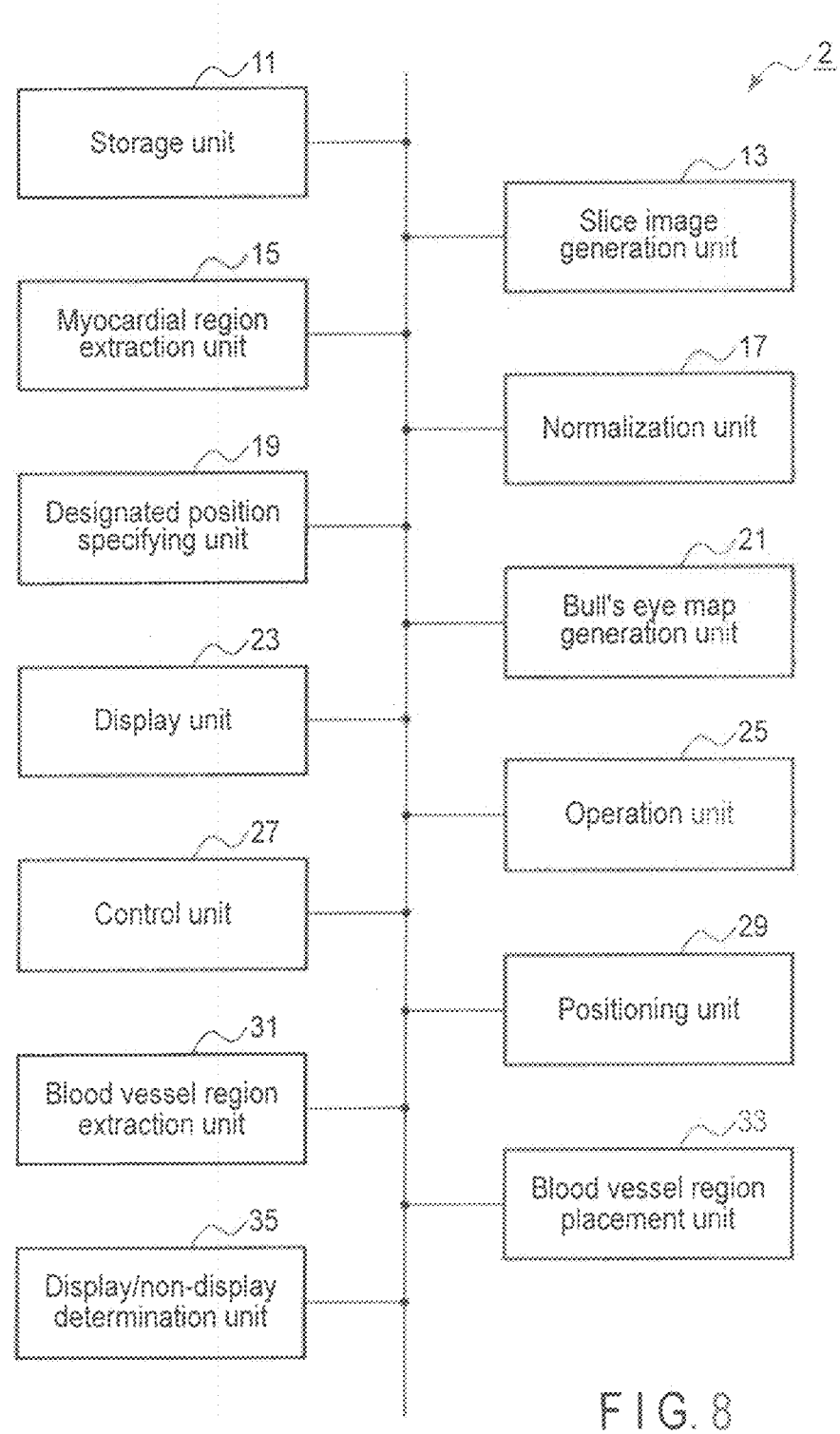
FIG. 8 is a block diagram showing the arrangement of a medical image processing apparatus according to the second embodiment.

FIG. 8 is a block diagram showing the arrangement of a medical image processing apparatus 2 according to the second embodiment. As shown in FIG. 8, the medical image processing apparatus 2 includes a storage unit 11, a slice image generation unit 13, a myocardial region extraction unit 15, a normalization unit 17, a designated position specifying unit 19, a bull's eye map generation unit 21, a display unit 23, an operation unit 25, a control unit 27, a positioning unit 29, a blood vessel region extraction unit 31, and a blood vessel region placement unit 33.

The storage unit 11 according to the second embodiment further stores three-dimensional morphological image data concerning morphological indices of the heart. As three-dimensional morphological image data, it is possible to use the data generated by medical image diagnostic apparatuses such as an X-ray computed tomography apparatus, magnetic resonance imaging apparatus, and ultrasonic diagnostic apparatus. Assume that in the following description, three-dimensional morphological image data according to the second embodiment is the volume data (to be referred to as CT volume data hereinafter) generated by scanning the heart injected with a contrast medium using multislice CT. A CT volume value as a kind of morphological index is assigned to CT volume data.

The positioning unit 29 positions myocardial SPECT data to CT volume data. Positioning will calculate positioning information for positioning the myocardial SPECT data to the CT volume data.

The blood vessel region extraction unit 31 extracts pixel regions concerning blood vessels (to be referred to as blood vessel regions hereinafter) from the CT volume data. A blood vessel region is typically a pixel region concerning a coronary artery (to be referred to as a coronary artery region hereinafter).

The blood vessel region placement unit 33 places, on the bull's eye map, the blood vessel regions expressing the spatial distribution of the extracted blood vessel regions by the same two-dimensional polar coordinate system as that of the bull's eye map. More specifically, the blood vessel region placement unit 33 calculates the positions of coronary artery regions defined by the same two-dimensional polar coordinate system as that of the bull's eye map. The blood vessel region placement unit 33 plots points in the pixel regions at the calculated positions of the coronary artery regions on the bull's eye map, thereby placing the coronary artery regions on the bull's eye map.

The display unit 23 according to the second embodiment displays a bull's eye map on which coronary artery regions are placed on the display device.

Myocardial browsing display processing according to the second embodiment which is performed under the control of the control unit 27 will be described in detail below. FIG. 9 is a flowchart showing a typical procedure for myocardial browsing display processing according to the second embodiment which is performed under the control of the control unit 27. Assume that a bull's eye map has already been generated by using the first embodiment at the start of myocardial browsing display processing according to the second embodiment.

As shown in FIG. 9, first of all, the control unit 27 causes the positioning unit 29 to perform positioning processing (step SB1). In step SB1, the positioning unit 29 positions myocardial SPECT data to CT volume data. Myocardial SPECT data and CT volume data sometimes differ in cardiac phase (diastolic phase, systolic phase, or the like) at the time of imaging. Typically, therefore, the left ventricular region included in myocardial SPECT data and that included in CT volume data differ in size. For this reason, the positioning unit 29 extracts anatomical feature points of the respective data and executes positioning by using the anatomical feature points. For example, as anatomical feature points, the cardiac apex portion and cardiac base portion of the left ventricular region are extracted. In this case, the positioning unit 29 calculates, as positioning information, for example, a coordinate conversion formula for conversion from the cardiac apex portion and cardiac base portion of the CT volume data to those of the myocardial SPECT data. The positioning unit 29 positions the myocardial SPECT data to the CT volume data by multiplying the CT volume data by this coordinate conversion formula.

Upon execution of step SB1, the control unit 27 causes the blood vessel region extraction unit 31 to perform blood vessel region extraction processing (step SB2). In step SB2, the blood vessel region extraction unit 31 extracts a coronary artery region from the CT volume data. More specifically, the blood vessel region extraction unit 31 applies a region growing method to the CT volume data to extract a coronary artery region. First of all, the blood vessel region extraction unit 31 sets a seed point in the coronary artery region of each short-axis slice image in accordance with operation by the user via the operation unit 25 or by image processing. The blood vessel region extraction unit 31 then searches for 26 voxels adjacent to the seed point, and integrates adjacent voxels satisfying an integration condition. An integration condition is set in the myocardial SPECT value range which the coronary artery can have. This operation extracts a pixel region satisfying the integration condition and coupled to the seed point, i.e., the coronary artery region.

Upon execution of step SB2, the control unit 27 causes the blood vessel region placement unit 33 to perform placement processing (step SB3). In step SB3, the blood vessel region placement unit 33 places the coronary artery region on the bull's eye map.

Figure 10:
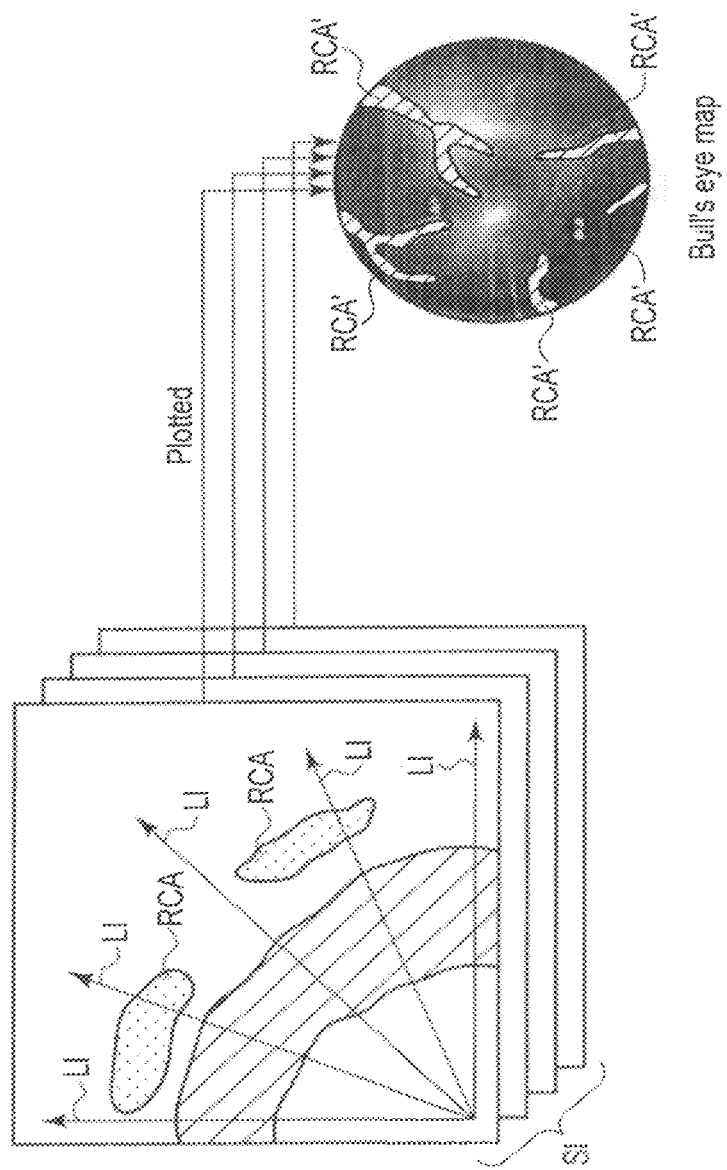
FIG. 10 is a view for explaining step SB3 in FIG. 9.

FIG. 10 is a view for explaining step SB3. More specifically, first of all, the blood vessel region placement unit 33 projects a coronary artery region RCA of the CT volume data onto each short-axis slice image IS of the myocardial SPECT data by using the coordinate conversion formula. The blood vessel region placement unit 33 then calculates the position of the coronary artery in the same polar coordinate system as that on the bull's eye map with respect to each short-axis slice image IS. The blood vessel region placement unit 33 then plots points representing the coronary artery region at the calculated position on the bull's eye map. A set of plotted points becomes a coronary artery region RCA' on the bull's eye map. More specifically, with regard to each straight line LI of each short-axis slice image IS, the blood vessel region placement unit 33 determines whether the coronary artery region RCA exists on the straight line LI. Upon determining that the coronary artery region RCA does not exist on the straight line LI, the blood vessel region placement unit 33 assigns no points representing the coronary artery region RCA' to the pixels of the bull's eye map which correspond to the straight line LI. Upon determining that the coronary artery region RCA exists on the straight line LI, the blood vessel region placement unit 33 assigns points representing the coronary artery region RCA' to the pixels of the bull's eye map which correspond to the straight line LI. This places the coronary artery region RCA' on the bull's eye map.

Upon executing step SB3, the control unit 27 causes the display unit 23 to perform display processing (step SB4). In step SB4, the display unit 23 displays the bull's eye map having the coronary artery region and generated in step SB3 on the display device. Placing the coronary artery region on the bull's eye map allows the user to easily comprehend an anatomical positional relationship on the bull's eye map.

Upon execution of step SB4, the control unit 27 terminates the myocardial SPECT browsing display processing according to the second embodiment.

Note that display/non-display of a local region in a coronary artery region on a bull's eye map may be switched accompanying a change in designated value. Display/non-display processing of a local region in a coronary artery region will be described below.

Figure 11:
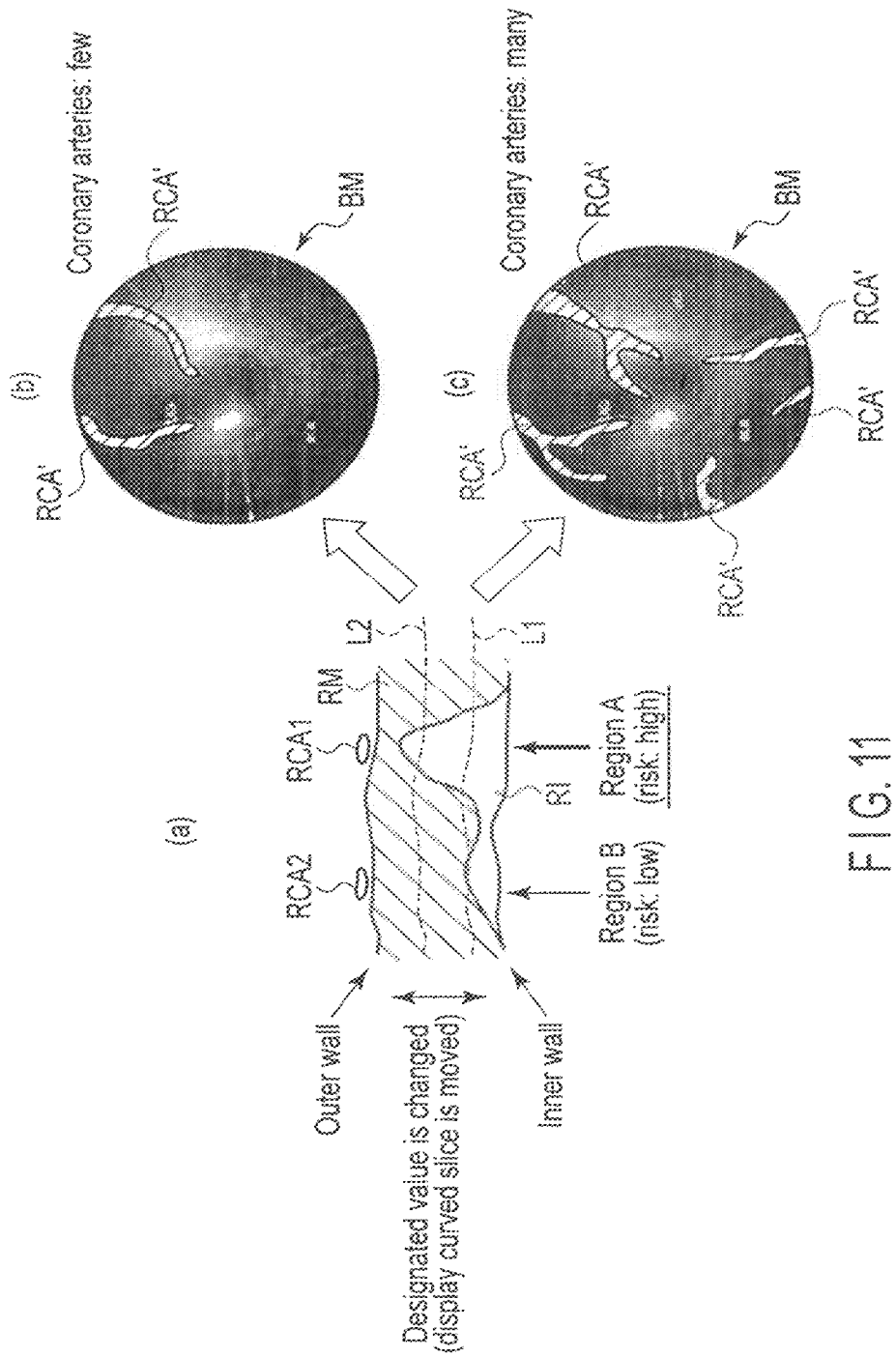
FIG. 11 is a view for explaining display/non-display processing of a local region of a coronary artery region, which is performed by a display/non-display determination unit and a blood vessel region placement unit in FIG. 8.

As shown in FIG. 8, for display/non-display processing of a local region in a coronary artery region, the medical image processing apparatus 2 further includes a display/non-display determination unit 35. FIG. 11 is a view for explaining display/non-display processing of a local region in a coronary artery region which is performed by the display/non-display determination unit 35 and the blood vessel region placement unit 33. In FIG. 11, (a) is a view schematically showing a myocardial region RM and its peripheral portion in a short-axis slice image (orthogonal coordinate system). A dotted line L1 represents a display curved slice of a bull's eye map which corresponds to a first designated value. The display curved slice corresponding to the first designated value is set near the inner wall. A dotted line L2 represents a display curved slice of a bull's eye map which corresponds to a first designated value. The display curved slice corresponding to the second designated value is set near the outer wall. The myocardial region RM includes a pixel region RI (to be referred to as an ischemic region hereinafter) concerning an ischemic region. An ischemic region is a myocardial region which is less infiltrated with blood than a normal region. The ischemic region is smaller in the accumulation of radioisotopes than the normal region. Therefore, the ischemic region is lower in myocardial SPECT value than the myocardial region concerning the normal region. In a region A, the ischemic region RI extends from the inner wall to a portion near the outer wall, and hence is clinically higher in risk than a region B. In FIG. 11, (b) shows a bull's eye map concerning a display curved slice L1. In FIG. 11, (b) shows a bull's eye map concerning a display curved slice L2.

With regard to each of a plurality of pixels included in a bull's eye map concerning a display curved slice corresponding to a designated value, the display/non-display determination unit 35 determines, based on the myocardial SPECT value of the pixel, whether to display a blood vessel region on the pixel. More specifically, with respect to each of a plurality of pixels of a bull's eye map, the display/non-display determination unit 35 determines whether the myocardial SPECT value of the pixel is equal to or more than a threshold. The threshold is set for a myocardial SPECT value that can discriminate a myocardial region concerning a normal region from an ischemic region.

If the display/non-display determination unit 35 determines that the myocardial SPECT value is equal to or less than the threshold, the blood vessel region placement unit 33 places points representing the coronary artery region RCA' on pixels of the bull's eye map. If the display/non-display determination unit 35 determines that myocardial SPECT value is equal to or more than the threshold, the blood vessel region placement unit 33 places no points representing the coronary artery region RCA' on pixels of the bull's eye map.

The display/non-display determination unit 35 and the blood vessel region placement unit 33 execute the above processing every time the user changes a designated value (display curved slice) via the operation unit 25. In this manner, every time a designated value (a display curved slice position on the bull's eye map) is changed, the display/non-display determination unit 35 and the blood vessel region placement unit 33 can switch between displaying and not displaying the coronary artery region on the bull's eye map for each local region. That is, a coronary artery region existing near a pixel region of myocardial SPECT values lower than the threshold is placed on the bull's eye map, while a coronary artery region existing near a pixel region of myocardial SPECT values higher than the threshold is erased from the bull's eye map. Placing a coronary artery region existing near a pixel region of myocardial SPECT values lower than the threshold on a bull's eye map in this manner allows the user to evaluate the clinical risk of each region.

As described above, the medical image processing apparatus 2 according to the second embodiment can achieve an improvement in the diagnostic performance of a bull's eye map.

(Third Embodiment)

A medical image processing apparatus according to the third embodiment superimposes and displays a curve representing the spatial distribution of display curved slices of a bull's eye map on a morphological image defined by an orthogonal coordinate system. The medical image processing apparatus according to the third embodiment will be described below. Note that the same reference numerals in the following description denote constituent elements having almost the same functions as those in the first and second embodiments, and a repetitive description will be made only when required.

Figure 12:
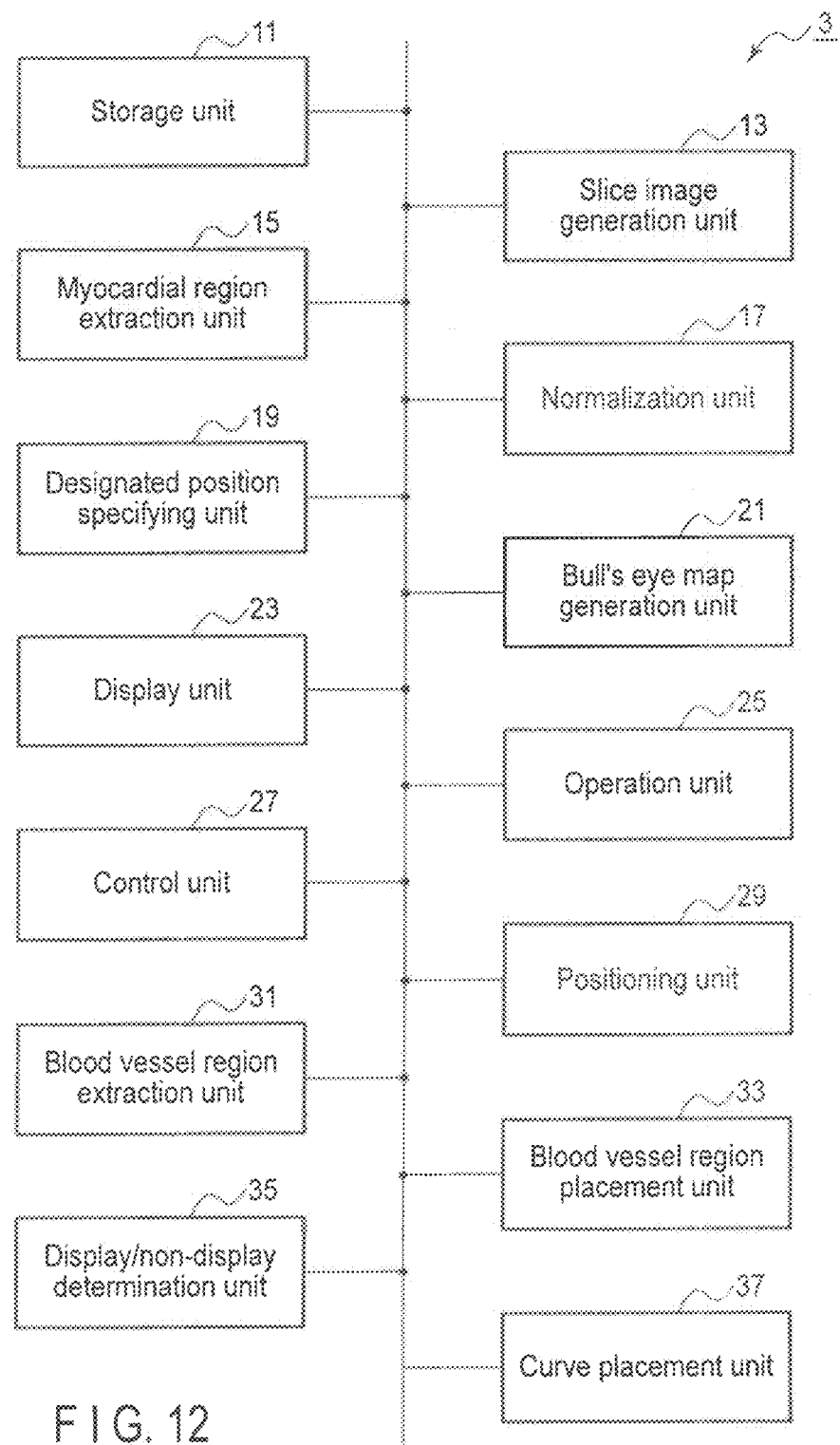
FIG. 12 is a block diagram showing the arrangement of a medical image processing apparatus according to the third embodiment.

FIG. 12 is a block diagram showing the arrangement of a medical image processing apparatus 3 according to the third embodiment. As shown in FIG. 12, the medical image processing apparatus 3 according to the third embodiment includes a storage unit 11, a slice image generation unit 13, a myocardial region extraction unit 15, a normalization unit 17, a designated position specifying unit 19, a bull's eye map generation unit 21, a display unit 23, an operation unit 25, a control unit 27, a positioning unit 29, a blood vessel region extraction unit 31, a blood vessel region placement unit 33, a display/non-display determination unit 35, and a curve placement unit 37.

The slice image generation unit 13 according to the third embodiment generates a slice image (to be referred to as a CT slice image hereinafter) concerning a slice (to be referred to as a CT slice hereinafter) intersecting a myocardial region based on CT volume data. A CT slice may have any position and direction as long as it intersects a myocardial region. The number of CT slices may be one or more.

The curve placement unit 37 calculates positions on a CT slice image of a display curved slice of a bull's eye map which corresponds to a designated value. The curve placement unit 37 plots points representing a curve at the calculated positions. This places a curve representing the spatial distribution of display curved slices of the bull's eye map on each CT slice image.

Figure 13:
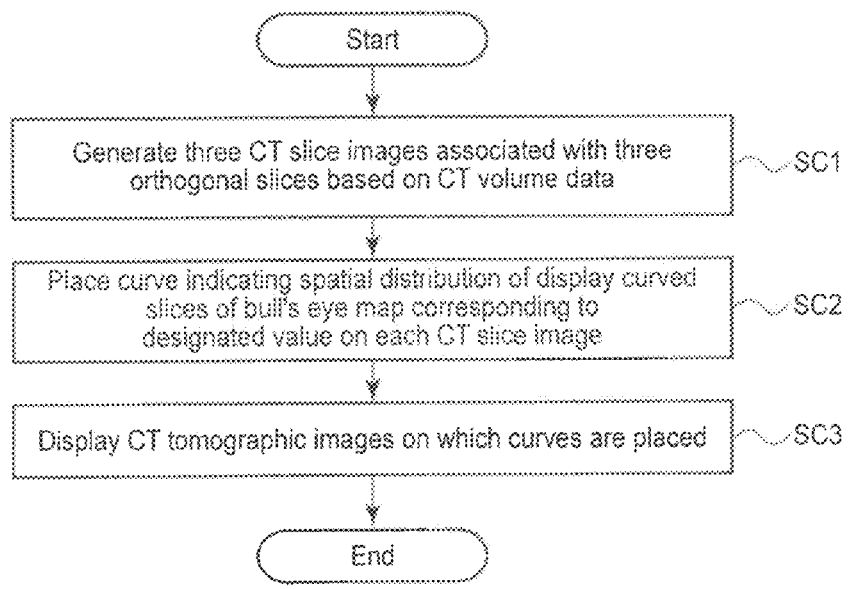
FIG. 13 is a flowchart showing a typical procedure for myocardial SPECT browsing display processing according to the third embodiment, which is performed under the control of a control unit in FIG. 12.

FIG. 13 is a flowchart showing a typical procedure for myocardial SPECT browsing display processing which is performed under the control of the control unit 27 according to the third embodiment. Assume that a bull's eye map has already been generated by using the first embodiment at the start of myocardial browsing display processing according to the third embodiment.

As shown in FIG. 13, the control unit 27 causes the slice image generation unit 13 to perform slice image generation processing (step SC1). In step SC1, the slice image generation unit 13 generates three CT slice images concerning three orthogonal slices based on CT volume data. More specifically, the slice image generation unit 13 sets a cardiac axis in CT volume data in the same manner as in step SA1. Upon setting a cardiac axis, the slice image generation unit 13 generates a slice image with reference to the cardiac axis. Myocardial SPECT frequently uses three orthogonal slices with reference to the cardiac axis in consideration of clinical utility. These three slices include a short-axis slice intersecting the cardiac axis at a right angle, a vertical long-axis slice parallely intersecting the cardiac axis, and a horizontal long-axis slice parallely intersecting the cardiac axis and perpendicular to the vertical long-axis slice. In this case, the slice image generation unit 13 performs MPR (multiplanar reconstruction) processing of the CT volume data to generate a CT slice image concerning the short-axis slice, a CT slice image concerning the vertical long-axis slice, and a CT slice image concerning the horizontal long-axis slice.

Upon executing step SC1, the control unit 27 causes the curve placement unit 37 to perform curve position calculation processing (step SC2). In step SC2, the curve placement unit 37 places a curve representing the spatial distribution of display curved slices of the bull's eye map corresponding to a designated value on each CT slice image. More specifically, first of all, the curve placement unit 37 calculates a position on each CT slice image of a display curved slice of the bull's eye map corresponding to a designated value based on positioning information for the myocardial SPECT data and the CT volume data calculated in step SB1. More specifically, first of all, the curve placement unit 37 specifies a plurality of pixels on the myocardial SPECT data forming a display curved slice based on a designated value. The curve placement unit 37 specifies a plurality of pixels of each CT slice image forming a display curved slice from the plurality of specified pixels by using the positioning information. When specifying a plurality of pixels, the curve placement unit 37 plots points for a curve on the plurality of specified pixels. This places a curve representing the spatial distribution of display curved slices on each CT slice image. Note that if points are not continuous but are spaced apart from each other, the points may be connected to each other by straight or curved lines.

Upon executing step SC2, the control unit 27 causes the display unit 23 to perform display processing (step SC3). In step SC3, the display unit 23 displays a CT slice image on which a curve representing the spatial distribution of display curved slices is arranged.

Figure 14:
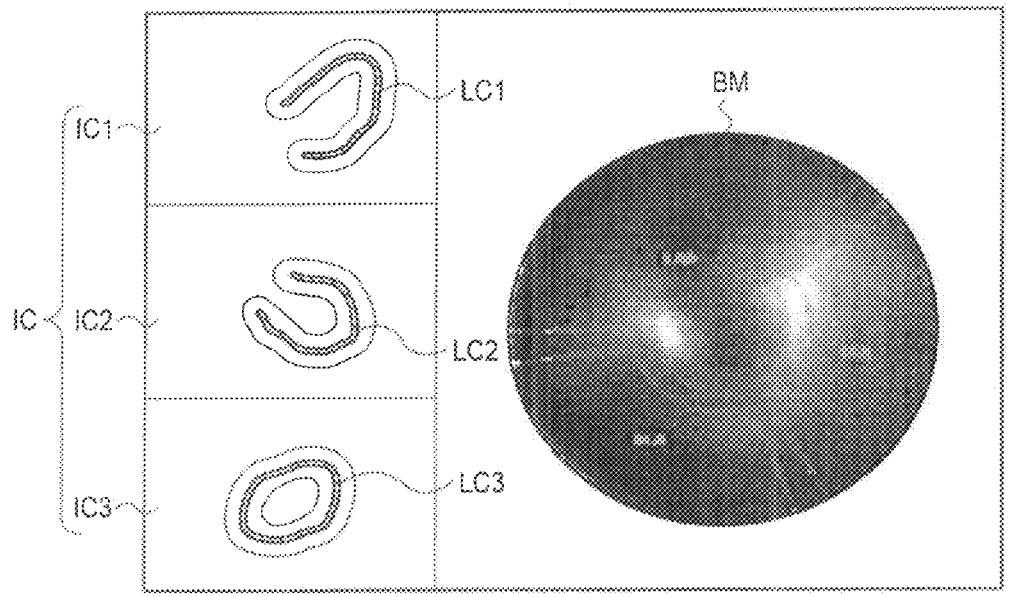
FIG. 14 is a view showing a display example of CT slice images on which curves representing the spatial distributions of display curved slices in step SC3 in FIG. 13.

FIG. 14 is a view showing a display example of CT slice images IC on which curves representing the spatial distributions of display curved slices are arranged. As shown in FIG. 14, there are arranged, on a display window, together with a bull's eye map BM, a CT slice image IC1 concerning a horizontal long-axis slice, a CT slice image IC2 concerning a vertical long-axis slice, and a CT slice image IC3 concerning a short-axis slice, all of which are generated in step SC1. Curves LC1, LC2, and LC3 representing the spatial distributions of display curved slices calculated in step S2 are respectively superimposed on the slice images IC1, IC2, and IC3. In this manner, a curve representing the spatial distribution of display curved slices of a bull's eye map is placed on a CT slice image as a kind of morphological image defined by an orthogonal coordinate system. This allows the user to easily comprehend the position of a display curved slice of the bull's eye map.

When the user has changed the designated value via the operation unit 25, the curve placement unit 37 moves the curve on the CT slice image in accordance with the changed designated value.

FIG. 15 is a view for explaining the movement of the curves LC1, LC2, and LC3 on the CT slice images IC1, IC2, and IC3 accompanying a change in designated value. As shown in FIG. 15, for example, it is preferable to change the designated value synchronously with the movement of an input device (mouse). The curve placement unit 37 calculates the changed designated value in real time in accordance with a drag amount and a dragging direction. The curve placement unit 37 then places a curve representing the spatial distribution of display curved slices of the bull's eye map corresponding to the changed designated value on each CT slice image in real time.

More specifically, when the mouse is dragged to the right in a specific region on a display window (or an application window), the curves LC1, LC2, and LC3 are moved on the CT slice images IC1, IC2, and IC3 toward the outer wall by a numerical value corresponding to the drag amount in the rightward direction. When the mouse is dragged to the left in the specific region on the display window (or the application window), the curves LC1, LC2, and LC3 are moved on the CT slice images IC1, IC2, and IC3 toward the inner wall by a numerical value corresponding to the drag amount in the leftward direction. It is preferable to set a specific region in a display region of the bull's eye map BM, from the viewpoint of the operability of designated value changing operation by the user.

Note that the designated value changing method to be used is not limited to the above method of changing a designated value synchronously with the movement of an input device. For example, the user may change a designated value by directly inputting a numerical value via an input device such as a keyboard or touch panel or moving the position of the knob on the slider bar.

In this manner, it is possible to change a designated value, i.e., move curves on CT slice images, via the operation unit 25, synchronously with a change in display curved slice of the bull's eye map.

As described above, the medical image processing apparatus according to the third embodiment can achieve an improvement in the diagnostic performance of a bull's eye map.

Various modifications of this embodiment will be described next.

(First Modification)

A medical image processing apparatus according to the first modification displays a plurality of bull's eye maps concerning a plurality of display curved slices in a multi-frame format. The medical image processing apparatus according to the first modification will be described below. Note that the same reference numerals in the following description denote constituent elements having almost the same functions as those in this embodiment, and a repetitive description will be made only when required.

Figure 16:
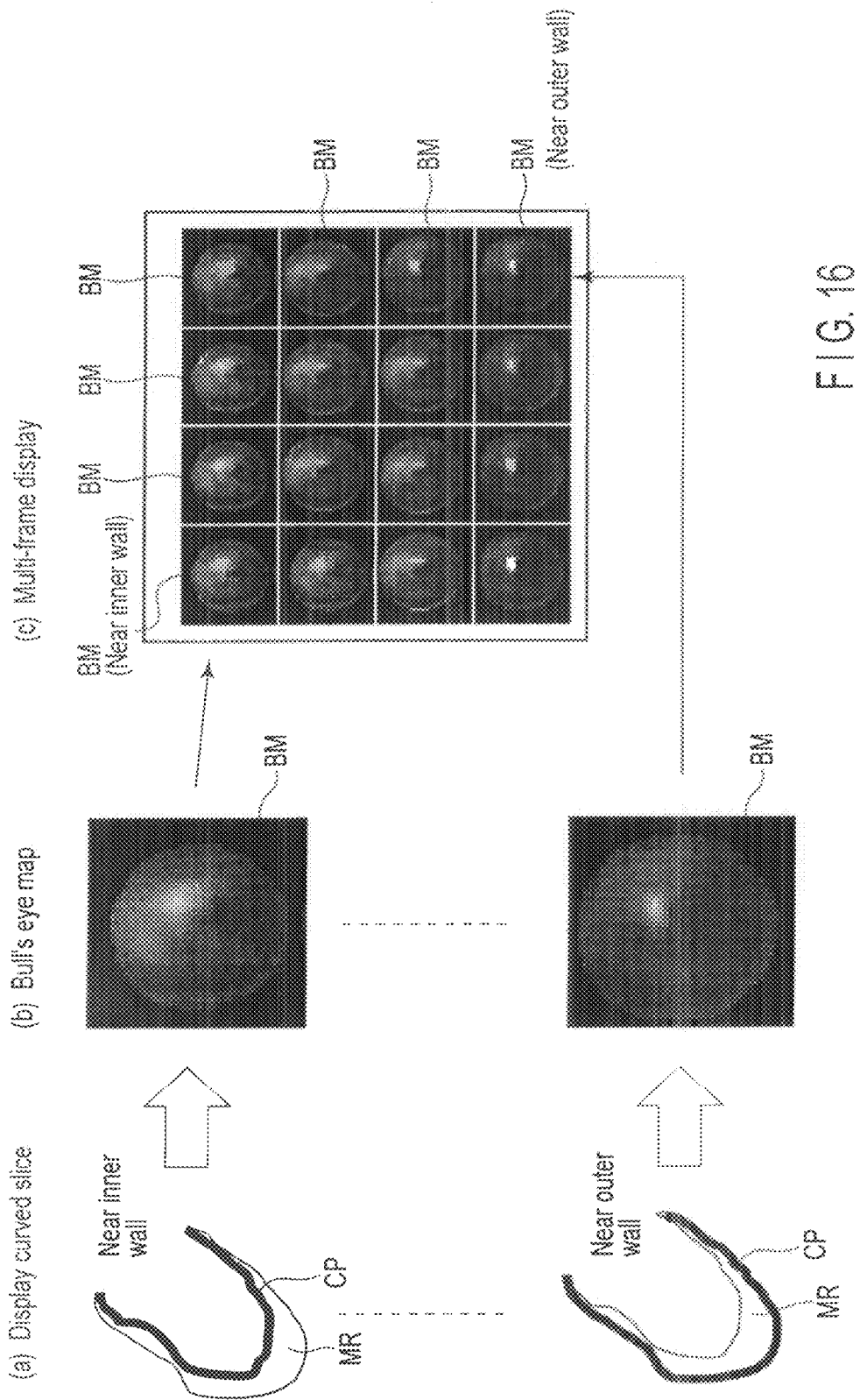
FIG. 16 is a view schematically showing a procedure for multi-frame display processing by a medical image processing apparatus according to the first modification.

FIG. 16 is a view schematically showing a procedure for multi-frame display processing by the medical image processing apparatus according to the first modification. The control unit 27 according to the first modification starts multi-frame display processing in response to a multi-frame display instruction issued by the user via the operation unit 25. As in this embodiment, the myocardial region extraction unit 15 extracts a myocardial region from myocardial SPECT data, and the normalization unit 17 normalizes the distance between the inner wall and outer wall of the myocardial region with a predetermined numerical value range.

As indicated by (a) in FIG. 16, for example, the designated position specifying unit 19 sets a plurality of display curved slices at different positions in the thickness direction in a myocardial region MR. Display curved slices CP are set at predetermined intervals between the inner wall and outer wall of the myocardial region MR normalized by the normalization unit 17. As indicated by (b) in FIG. 16, the bull's eye map generation unit 21 generates a plurality of bull's eye maps BM respectively corresponding to the plurality of display curved slices CP based on myocardial SPECT data. As indicated by (c) in FIG. 16, the display unit 23 displays the plurality of bull's eye maps BM respectively corresponding to the plurality of display curved slices CP on a window in the multi-frame format. More specifically, the plurality of bull's eye maps BM are sequentially displayed on the window in the order from the inner wall side to the outer wall side. In other words, the plurality of bull's eye maps BM concerning different display curved slices are displayed side by side on one window.

Displaying a plurality of bull's eye maps in the multi-frame format in this manner allows the user to observe the plurality of bull's eye maps in the form of a list.

As described above, the medical image processing apparatus according to the first modification can achieve an improvement in the diagnostic performance of a bull's eye map.

(Second Modification)

A medical image processing apparatus according to the second modification displays a three-dimensional bull's eye map. The medical image processing apparatus according to the second modification will be described below. Note that the same reference numerals in the following description denote constituent elements having almost the same functions as those in this embodiment, and a repetitive description will be made only when required.

Figure 17:
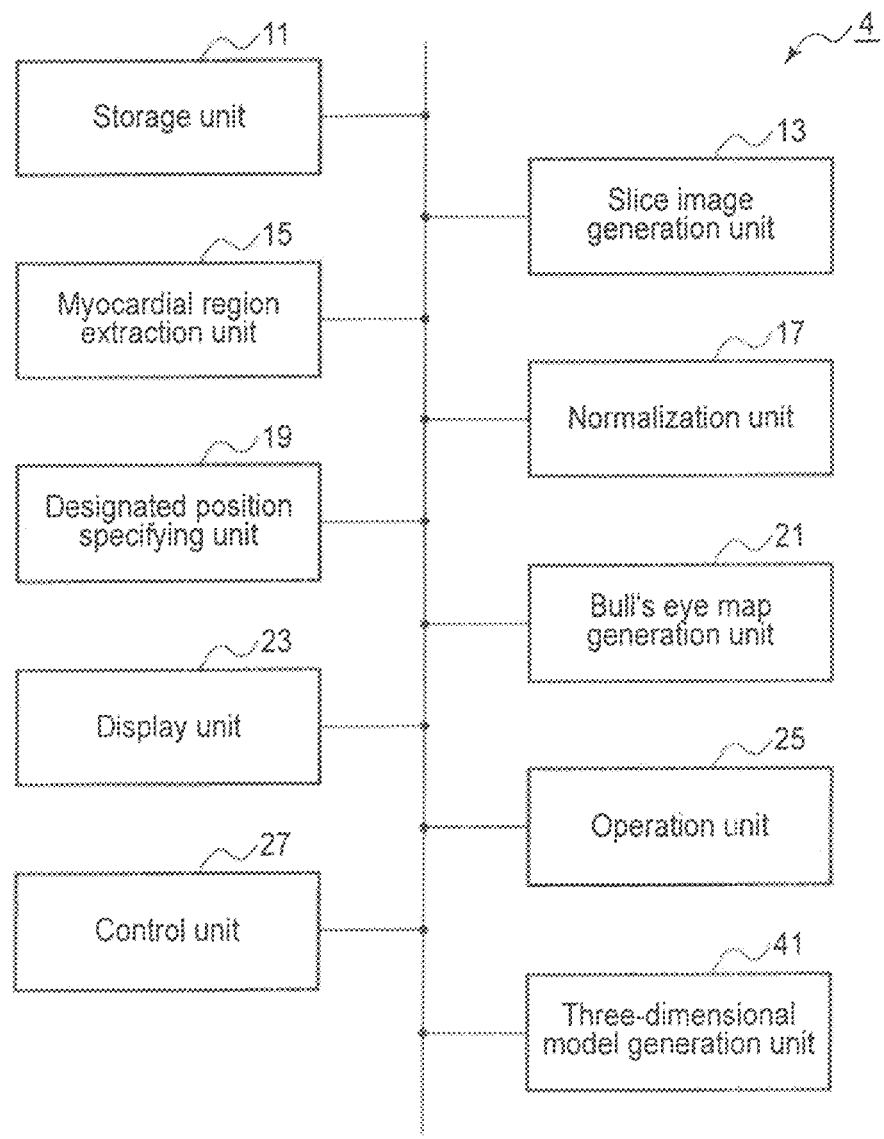
FIG. 17 is a block diagram showing the arrangement of a medical image processing apparatus according to the second modification.

FIG. 17 is a block diagram showing the arrangement of a medical image processing apparatus 4 according to the second modification. As shown in FIG. 17, the medical image processing apparatus 4 includes a storage unit 11, a slice image generation unit 13, a myocardial region extraction unit 15, a normalization unit 17, a designated position specifying unit 19, a bull's eye map generation unit 21, a display unit 23, an operation unit 25, a control unit 27, and a three-dimensional model generation unit 41.

The three-dimensional model generation unit 41 generates a three-dimensional model image expressing the spatial distribution of myocardial SPECT values in a myocardial region by using three-dimensional coordinates unique to the second modification based on myocardial SPECT data. Three-dimensional coordinates unique to the second modification are defined by two-dimensional polar coordinates and the normalized heights between the inner wall and the outer wall. Two-dimensional polar coordinates are defined with the same polar coordinate system as that of the bull's eye map. A height is defined by, for example, the normalized numerical value of a display curved slice of a bull's eye map or the number of slices from a bull's eye map corresponding to the inner wall or outer wall. An image processing space expressed by three-dimensional coordinates will be referred to as a three-dimensional model space hereinafter.

Three-dimensional model image generation processing performed by the three-dimensional model generation unit 41 according to the second modification will be described next.

FIG. 18 is a view schematically showing a typical procedure for three-dimensional bull's eye map generation processing performed by the three-dimensional model generation unit 41. Assume that as indicated by (a) in FIG. 18, the bull's eye map generation unit 21 has generated a plurality of bull's eye maps BM at different positions in the thickness direction. The three-dimensional model generation unit 41 extracts a visualization target region from a plurality of bull's eye maps BM by threshold processing or the like. A visualization target region may be any region in which the user has a clinical interest. For the sake of a concrete description to be made below, however, assume that a visualization target region is an ischemic region. In this case, the three-dimensional model generation unit 41 extracts an ischemic region IR from the plurality of bull's eye maps BM by threshold processing or the like.

Typically, the ischemic region IR is formed so as to extend from the inner wall to the outer wall. Therefore, the height of the ischemic region IR in three-dimensional model data expresses Transmural Extent (an index concerning the spread of an ischemic region in the wall thickness direction). Transmural Extent is used as an index of the seriousness of a myocardial infarct in a clinical field.

As indicated by (b) in FIG. 18, the three-dimensional model generation unit 41 specifies the polar coordinates and height coordinates of the respective pixels included in the ischemic region IR and assigns voxel values to the voxels in a three-dimensional model space corresponding to the specified polar coordinates and height coordinates. The voxels to be assigned may be myocardial SPECT values or a specified value (e.g., "1") indicating a voxel belonging to the ischemic region IR. Assigning the pixel values of all the pixels in the ischemic region IR to a three-dimensional model space in this manner will generate three-dimensional model data MD. Transmural Extent is represented by a bar graph extending from the inner wall to the outer wall in the three-dimensional model data MD.

In order to facilitate comprehension of a positional relationship, it is preferable to arrange a schematic outer wall MAO and a schematic inner wall MAI in three-dimensional model data MD upon positional matching, as indicated by (b) in FIG. 18. The schematic outer wall MAO and the schematic inner wall MAI may be a bull's eye map BMO concerning a display curved slice of the outer wall and a bull's eye map BMi concerning a display curved slice of the inner wall. In addition, the schematic outer wall MAO and the schematic inner wall MAI may not be arranged.

The three-dimensional model generation unit 41 generates a three-dimensional model image for display by performing existing rendering processing for the three-dimensional model data. It is possible to set a point of view and a line of sight in rendering to an arbitrary position and direction. However, in order to facilitate comprehension of a positional relationship, a user such as a doctor may initially set a point of view and a line of sight so as to place a diaphragm portion or the like on the front side of a window. The display unit 23 displays the generated three-dimensional model image.

Observing a three-dimensional model image based on three-dimensional model data allows the user to easily comprehend Transmural Extent on the image.

According to the above description, a three-dimensional model image is generated from myocardial SPECT data via a plurality of bull's eye maps. However, a three-dimensional model image according to the second modification may be directly generated from myocardial SPECT data without via a plurality of bull's eye maps.

Figure 19:
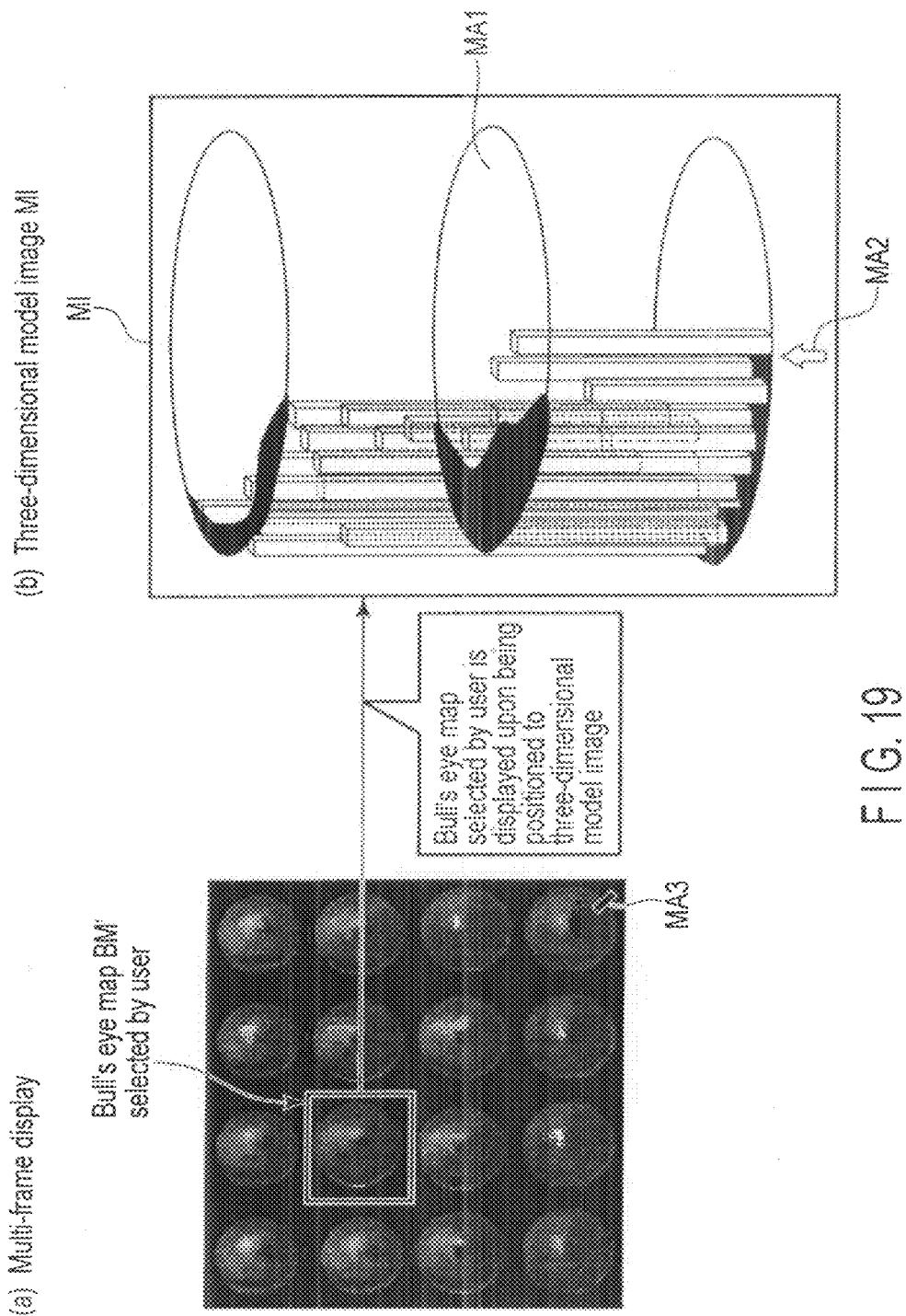
FIG. 19 is a view showing an application example of display of the three-dimensional model image displayed by a display unit in FIG. 17.

An application of display of a three-dimensional model image will be described next with reference to FIG. 19. As shown in FIG. 19, the display unit 23 superimposes and displays the position of a currently displayed bull's eye map on a three-dimensional model image MI. More specifically, the display unit 23 displays a plurality of bull's eye maps at different positions in the thickness direction in the multiframe format as in the first modification. The user selects a bull's eye map to be observed via the operation unit 25. The display unit 23 displays a selected bull's eye map BM in the original size. In addition, the display unit 23 displays the position of a selected bull's eye map BM' on the three-dimensional model image MI. More specifically, the display unit 23 specifies the height coordinates of the selected bull's eye map BM' and superimposes and displays a mark MA1 of the bull's eye map BM' on the three-dimensional model image MI at the specified height coordinates.

In order to facilitate comprehension of the positional relationship between the three-dimensional model image MI and the bull's eye map BM, it is preferable to respectively display marks MA2 and MA3 on the three-dimensional model image MI and the bull's eye map BM. The mark MA2 indicates the reference position of the three-dimensional model image MI. Typically, the reference position coincides with a front face of the three-dimensional model image MI. The mark MA3 indicates a position corresponding to the mark MA2. If, for example, the mark MA2 indicates a front face of the three-dimensional model image MI, the mark MA3 indicates a position on the bull's eye map BM which corresponds to the front face of the three-dimensional model image MI. Note that a reference position is not limited to the front face of the three-dimensional model image MI, and may be an anatomical reference point generally used in observation of a bull's eye map.

In order to improve the readability of a three-dimensional model image, an ischemic region may be exclusively displayed in a region of interest. For example, it is preferable for the user to set a region of interest on the schematic outer or inner wall of the three-dimensional model image MI via the operation unit 25. The display unit 23 erases an ischemic region which does not belong to polar coordinates in a region of interest from a three-dimensional model image and renders only an ischemic region belonging to polar coordinates in the region of interest into a three-dimensional mode image. This makes it possible to render only an ischemic region, in which the user is more interested, into a three-dimensional model image.

In addition, as in the second embodiment, a blood vessel region may be superimposed on the schematic outer or inner wall of a three-dimensional model image. For example, the display unit 23 preferably displays a blood vessel region in a region whose Transmural Extent value is larger than a threshold (for example, a blood vessel region of a coronary artery). Furthermore, it is preferable to allow to switch between ON and OFF of display of a blood vessel region in accordance with an instruction from the operation unit 25. This allows the user to, for example, easily recognize the association between the coronary artery and myocardial infarct.

As described above, the medical image processing apparatus according to the second modification can achieve an improvement in the diagnostic performance of a bull's eye map.

(Third Modification)

A medical image processing apparatus according to the third modification displays an annular image visualizing information in the cardiac wall thickness direction in a display form different from that of a bull's eye map. The medical image processing apparatus according to the third modification will be described below. Note that the same reference numerals in the following description denote constituent elements having almost the same functions as those in this embodiment, and a repetitive description will be made only when required.

FIG. 20 is a view showing the arrangement of a medical image processing apparatus 5 according to the third modification. As shown in FIG. 20, the medical image processing apparatus 4 includes a storage unit 11, a slice image generation unit 13, a myocardial region extraction unit 15, a normalization unit 17, a designated position specifying unit 19, a bull's eye map generation unit 21, a display unit 23, an operation unit 25, a control unit 27, and an image processing unit 51.

The image processing unit 51 generates an image (annular image) expressing the distribution of pixel values in a myocardial region in a schematic annular shape based on myocardial SPECT data. The display unit 23 displays the annular image.

FIG. 21 is a view for explaining annular image generation processing by the image processing unit 51. As shown in FIG. 21, the image processing unit 51 sets a plurality of slices CSn perpendicular to a cardiac axis AC in myocardial SPECT data. For example, FIG. 21 shows five slices CS1, CS2, CS3, CS4, and CS5. A myocardial region MR on each slice CSn has an almost annular shape. The image processing unit 51 standardizes (scales) the shape of the myocardial region MR on each slice CSn into a preset annular shape. In other words, the image processing unit 51 assigns the pixel value of each pixel of the myocardial region MR on each slice CSn to corresponding pixels on the annular model. The annular models have larger diameters as the distance from the cardiac apex portion increases. An annular image is generated by arranging the respective annular models so as to match their centers with each other.

Figure 22:
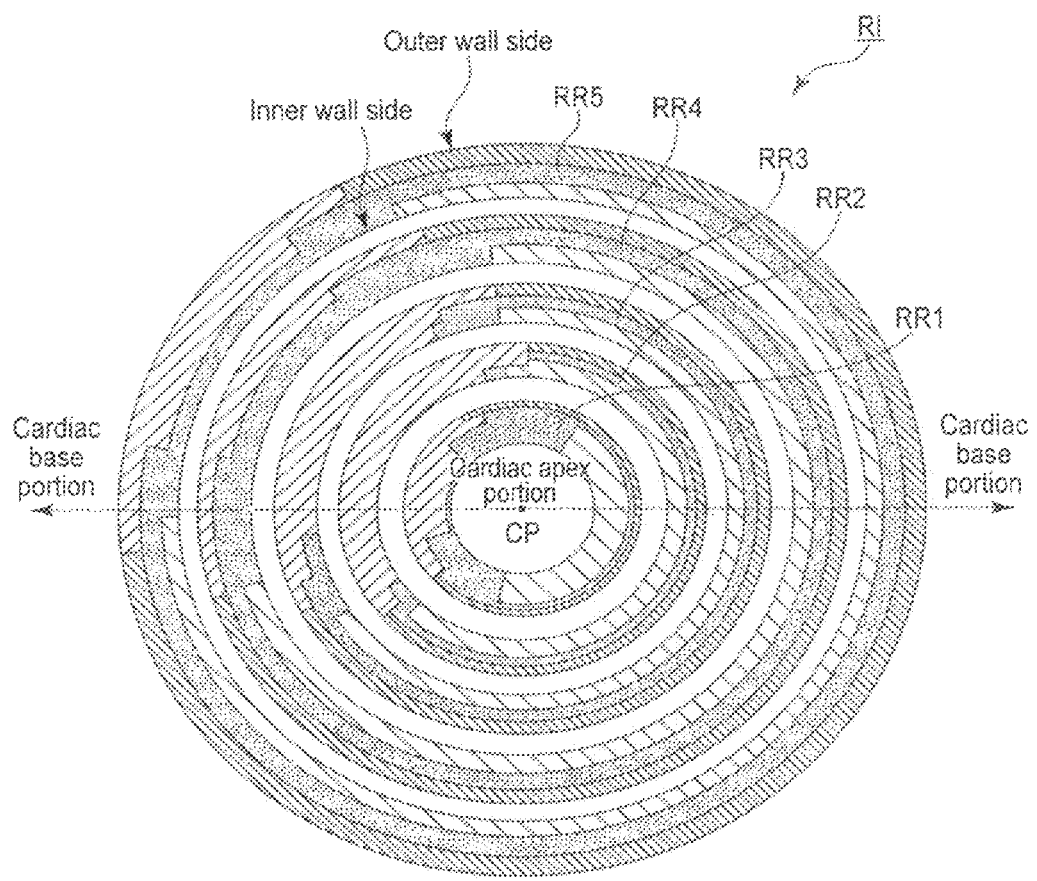
FIG. 22 is a view showing an example of the annular image generated by the image processing unit in FIG. 20.

FIG. 22 is a view showing an example of an annular image RI generated by the image processing unit 51. As shown in FIG. 22, the annular image RI includes a plurality of annular regions RRn respectively corresponding to a plurality of slices. FIG. 22 shows five annular regions RR1, RR2, RR3, RR4, and RR5 in correspondence with FIG. 21. The plurality of annular regions RRn are concentric circular rings sharing a center CP. The respective annular regions RRn are standardized so as not to spatially overlap. Each annular region RRn is defined by a two-dimensional orthogonal coordinate system. For example, the inner edge of each annular region RRn corresponds to the inner wall of the myocardial region, and the outer edge of each annular region RRn corresponds to the outer wall of the myocardial region.

In this manner, annular images can express the spatial distribution of pixel values on a plurality of slices arranged along the cardiac axis by using a standardized orthogonal coordinate system. This makes it possible to easily comprehend the distribution of myocardial SPECT values in the cardiac wall thickness direction. In addition, since the shape of a myocardial region on an annular image is standardized to a standard annular model, it is possible to easily comprehend an anatomical positional relationship without the influences of individual differences, examination conditions, and the like.

The image processing unit 51 can generate an image (three-dimensional annular image) three-dimensionally expressing the distribution of pixel values in a myocardial region by a schematic annular shape based on myocardial SPECT data. The display unit 23 displays the three-dimensional annular image.

FIG. 23 is a view showing an example of a three-dimensional annular image RI' generated by the image processing unit 51. A plurality of annular regions RRn in the three-dimensional annular image RI' are arranged along a cardiac axis AC in accordance with positions in a cardiac axis AC direction. It is preferable to arbitrarily set the point of view and line of sight of the three-dimensional annular image RI' in accordance with instructions issued by the user via the operation unit 25. For example, it is preferable to set a point of view and a line of sight so as to allow to view the plurality of annular regions RRn obliquely downward, as shown in FIG. 23. Each annular region RRn may be generated by MIP thick in the cardiac axis direction. This allows the display unit 23 to simultaneously display the spatial distribution of myocardial SPECT values in the cardiac axis direction. The user can observe the distribution of myocardial SPECT values in all directions by rotating the point of view around the cardiac axis AC via the operation unit 25.

In addition, the image processing unit 51 can generate a cup model image based on myocardial SPECT data. FIG. 24 is a view showing an example of a cup model image CMI generated by the image processing unit 51. As shown in FIG. 24, the cup model image CMI is generated by assigning the myocardial SPECT values of the inner and outer walls to a three-dimensional model in the form of a cup which has a schematic myocardial shape. It is preferable to arbitrarily set the point of view and light of sight of the cup model image CMI in accordance with instructions issued by the user via the operation unit 25. This allows the user to observe the distribution of myocardial SPECT values in all directions by rotating the point of view around the cardiac axis AC via the operation unit 25.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
   a storage unit configured to store three-dimensional function image data concerning a function index of a heart;
   a first extraction unit configured to extract a myocardial region from the three-dimensional function image data;
   a normalization unit configured to normalize a distance between an inner wall and outer wall of the myocardial region with a predetermined numerical value range associated with a thickness direction;
   a bull's eye map generation unit configured to generate a bull's eye map expressing a spatial distribution of pixel values at positions on the myocardial region by two-dimensional polar coordinates, the positions corresponding to predetermined values in the predetermined numerical value range;
   a designation unit configured to designate the predetermined values within the predetermined numerical value range, which is associated with the thickness direction, in accordance with an instruction from a user; and
   a display unit configured to display the bull's eye map.

2. The medical image processing apparatus of claim 1, further comprising a specifying unit configured to specify positions on the myocardial region which correspond to the predetermined values in the predetermined numerical value range,
   wherein the bull's eye map generation unit generates the bull's eye map in accordance with pixel values at the specified positions.

3. The medical image processing apparatus of claim 2, further comprising a slice image generation unit configured to generate a plurality of slice images arranged along a cardiac axis connecting a cardiac apex portion and a cardiac base portion based on the three-dimensional function image data,
   wherein the first extraction unit extracts each of a plurality of myocardial regions from the plurality of slice images,
   the normalization unit normalizes a distance between an inner wall and outer wall of each of the plurality of myocardial regions with a predetermined numerical value range, and
   the specifying unit specifies each position on each of the plurality of myocardial regions which corresponds to a designated value designated by the user within the predetermined numerical value range.

4. The medical image processing apparatus of claim 1, further comprising:
   a positioning unit configured to position three-dimensional morphological image data concerning a morphological index to the three-dimensional function image data in accordance with an anatomical feature point;

a second extraction unit configured to extract a blood vessel region from the three-dimensional morphological image data; and a placement unit configured to place, on the bull's eye map, a blood vessel region expressing a spatial distribution of the extracted blood vessel region by a two-dimensional polar coordinate system, wherein the display unit displays a bull's eye map on which the blood vessel region is placed.

5. The medical image processing apparatus of claim 4, further comprising a determination unit configured to determine, in accordance with a pixel value of each of a plurality of pixels included in the bull's eye map, whether to display the blood vessel region on each of the pixels, wherein the placement unit places the blood vessel region on the pixel on the bull's eye map, if the blood vessel region is determined to be displayed, and does not place the blood vessel region on the pixel on the bull's eye map, if the blood vessel region is determined not to be displayed.

6. The medical image processing apparatus of claim 1, further comprising:

a slice image generation unit configured to generate a slice image based on three-dimensional morphological image data concerning a morphological index; and a placement unit configured to place, on the slice image, a curve representing a spatial distribution of display curved slices of the bull's eye map corresponding to the designated value, wherein the display unit displays the bull's eye map on which the curve is placed.

7. The medical image processing apparatus of claim 1, wherein the bull's eye map generation unit generates a plurality of bull's eye maps respectively corresponding to a plurality of predetermined values in the predetermined numerical value range, and the display unit displays the plurality of bull's eye maps side by side.

8. The medical image processing apparatus of claim 1, further comprising a three-dimensional model image generation unit configured to generate a three-dimensional model image expressing a spatial distribution of pixel values in the myocardial region by three-dimensional coordinates defined by two-dimensional polar coordinates and normalized heights from an inner wall to an outer wall, wherein the display unit displays the three-dimensional model image.

* * * * *